(12) United States Patent
Gao et al.

(10) Patent No.: US 11,098,150 B2
(45) Date of Patent: Aug. 24, 2021

(54) BLOCK COPOLYMER AND MICELLE COMPOSITIONS AND METHODS OF USE THEREOF

(71) Applicant: The Board of Regents of the University of Texas System, Austin, TX (US)

(72) Inventors: Jinming Gao, Plano, TX (US); David Boothman, Dallas, TX (US); Kejin Zhou, Dallas, TX (US); Xiaonan Huang, Beijing (CN); Yiguang Wang, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 16/006,885

(22) Filed: Jun. 13, 2018

(65) Prior Publication Data
US 2018/0291134 A1    Oct. 11, 2018

Related U.S. Application Data

(63) Continuation of application No. 15/662,184, filed on Jul. 27, 2017, now Pat. No. 10,017,598, which is a
(Continued)

(51) Int. Cl.
| | | |
|---|---|---|
| *A61K 49/00* | (2006.01) | |
| *C08F 293/00* | (2006.01) | |
| *C07D 311/92* | (2006.01) | |
| *A61K 47/58* | (2017.01) | |
| *A61K 47/62* | (2017.01) | |
| *A61K 9/127* | (2006.01) | |
| *A61K 31/352* | (2006.01) | |
| *A61P 35/00* | (2006.01) | |
| *C08F 299/02* | (2006.01) | |
| *A61K 47/69* | (2017.01) | |
| *C08G 81/02* | (2006.01) | |

(Continued)

(52) U.S. Cl.
CPC ........ *C08F 293/005* (2013.01); *A61K 9/1075* (2013.01); *A61K 9/1273* (2013.01); *A61K 9/5031* (2013.01); *A61K 31/337* (2013.01); *A61K 31/352* (2013.01); *A61K 31/704* (2013.01); *A61K 47/58* (2017.08); *A61K 47/62* (2017.08); *A61K 47/6811* (2017.08); *A61K 47/6845* (2017.08); *A61K 47/6907* (2017.08); *A61K 49/0032* (2013.01); *A61K 49/0054* (2013.01); *A61K 49/0056* (2013.01); *A61K 49/0082* (2013.01); *A61P 35/00* (2018.01); *C07D 311/92* (2013.01); *C08F 299/024* (2013.01); *C08G 81/025* (2013.01); *G01N 33/582* (2013.01); *A61K 49/005* (2013.01); *C08F 220/34* (2013.01); *C08F 2438/01* (2013.01)

(58) Field of Classification Search
CPC .......................... A61K 49/005; A61K 49/0054
See application file for complete search history.

(56) References Cited

U.S. PATENT DOCUMENTS

| | | | |
|---|---|---|---|
| 6,660,793 B1 | 12/2003 | McIntyre et al. | |
| 9,751,970 B2 | 9/2017 | Gao et al. | |

(Continued)

FOREIGN PATENT DOCUMENTS

| | | |
|---|---|---|
| CS | 225516 | 6/1983 |
| GB | 475131 | 11/1937 |

(Continued)

OTHER PUBLICATIONS

Alani et al., "Polymeric micelles for the pH-dependent controlled, continuous low dose release of paclitaxel," *Biomaterials*, 31:1765-772, 2010.

(Continued)

*Primary Examiner* — James W Rogers
(74) *Attorney, Agent, or Firm* — Parker Highlander PLLC

(57) ABSTRACT

Provided herein are block copolymers comprising a hydrophilic polymer segment and a hydrophobic polymer segment, wherein the hydrophilic polymer segment comprises a polymer selected from the group consisting of: poly(ethylene oxide) (PEO), poly(methacrylate phosphatidyl choline) (MPC), and polyvinylpyrrolidone (PVP), wherein the hydrophobic polymer segment comprises

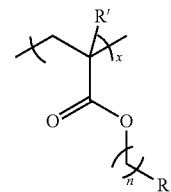

wherein R' is —H or —CH$_3$, wherein R is —NR$^1$R$^2$, wherein R$^1$ and R$^2$ are alkyl groups, wherein R$^1$ and R$^2$ are the same or different, wherein R$^1$ and R$^2$ together have from 5 to 16 carbons, wherein R$^1$ and R$^2$ may optionally join to form a ring, wherein n is 1 to about 10, and wherein x is about 20 to about 200 in total. Also provided are pH-sensitive micelle compositions for therapeutic and diagnostic applications.

15 Claims, 18 Drawing Sheets

Related U.S. Application Data continuation of application No. 15/072,522, filed on Mar. 17, 2016, now Pat. No. 9,751,970, which is a continuation of application No. 13/825,518, filed as application No. PCT/US2011/001418 on Aug. 11, 2011, now abandoned.

(60) Provisional application No. 61/471,054, filed on Apr. 1, 2011, provisional application No. 61/470,441, filed on Mar. 31, 2011, provisional application No. 61/385,422, filed on Sep. 22, 2010.

(51) Int. Cl.

| | | |
|---|---|---|
| G01N 33/58 | (2006.01) | |
| A61K 9/50 | (2006.01) | |
| A61K 31/337 | (2006.01) | |
| A61K 31/704 | (2006.01) | |
| A61K 9/107 | (2006.01) | |
| A61K 47/68 | (2017.01) | |
| C08F 220/34 | (2006.01) | |

(56) References Cited

U.S. PATENT DOCUMENTS

| | | |
|---|---|---|
| 10,017,598 B2 | 7/2018 | Gao et al. |
| 2006/0034796 A1 | 2/2006 | Ashwell et al. |
| 2006/0229235 A1 | 10/2006 | Peterson |
| 2008/0081075 A1 | 4/2008 | Hsiue et al. |
| 2009/0028788 A1 | 1/2009 | Achilefu |
| 2009/0317802 A1 | 12/2009 | Bhatia et al. |
| 2010/0069726 A1 | 3/2010 | Levinson |
| 2010/0303731 A1 | 12/2010 | Hyde et al. |
| 2010/0311903 A1 | 12/2010 | Rajagopalan |
| 2011/0305660 A1 | 12/2011 | Stayton et al. |
| 2012/0070399 A1 | 3/2012 | Jegou |
| 2013/0330278 A1 | 12/2013 | Gao et al. |
| 2013/0331426 A1 | 12/2013 | Gao et al. |

FOREIGN PATENT DOCUMENTS

| | | |
|---|---|---|
| GB | 1174148 | 12/1969 |
| WO | WO 2002/100439 | 12/2002 |
| WO | WO 2003/074026 | 9/2003 |
| WO | WO 2009/095569 | 8/2009 |
| WO | WO 2009/138473 | 11/2009 |
| WO | WO 2009/140429 | 11/2009 |
| WO | WO 2010/116063 | 10/2010 |
| WO | WO 2011/097384 | 8/2011 |
| WO | WO 2012-039741 | 3/2012 |
| WO | WO 2012/039855 | 3/2012 |
| WO | WO 2012/040513 | 3/2012 |

OTHER PUBLICATIONS

Albertazzi et al., "Delivery and subcellular targeting of dendrimer-based fluorescent pH sensors in living cells," *J Am Chem Soc.*, 132:18158-67, 2010.

Almutairi et al., "Biodegradable pH-sensing dendritic nanoprobes for near-infrared fluorescence lifetime and intensity imaging," *J Am Chem Soc.*, 130:444-5, 2008.

Bae et al., "Design of environment-sensitive supramolecular assemblies for intracellular drug delivery: polymeric micelles that are responsive to intracellular pH change," *Angew Chem Int Ed Engl.*, 42:4640-4643, 2003.

Bae et al., "Multifunctional polymeric micelles with folate-mediated cancer cell targeting and pH-triggered drug releasing properties for active intracellular drug delivery," *Mol BioSyst.*, 1:242-250, 2005.

Bae et al., "Preparation and Biological Characterization of Polymeric Micelle Drug Carriers with Intracellular pH-Triggered Drug Release Property: Tumor Permeability, Controlled Subcellular Drug Distribution, and Enhanced in Vivo Antitumor Efficacy," *Bioconjug Chem.*, 16:122-30, 2005.

Benjaminsen et al., "Evaluating nanoparticle sensor design for intracellular pH measurements," *ACS Nano*, 5:5864-73, 2011.

Blanco et al., "β-Lapachone-containing PEG-PLA Polymer Micelles as Novel Nanotherapeutics against NQO1-Overexpressing Tumor Cells," *J Control Release*, 122(3):365-374, 2007.

Braunecker et al., "Controlled/living radical polymerization: Features, developments, and perspectives," *Progress in Polymer Science*, 32(1):93-146, 2007.

Bütün et al., "Synthesis and aqueous solution properties of near-monodisperse tertiary amine methacrylate homopolymers and diblock copolymers," *Polymer*, 42:5993-6008, 2001.

Casey et al., "Sensors and regulators of intracellular pH," *Nat Rev Mol Cell Biol.*, 11:50-61, 2010.

Chenna et al., "Preparation and cytotoxicity toward cancer cells of mono(arylimino) derivatives of beta-lapachone," *J Med Chem.*, 44:2486-2489, 2001.

De Silva et al., "Signaling recognition events with fluorescent sensors and switches," *Chem Rev.*, 97:1515-1566, 1997.

Diaz-Fernandez et al., "Micelles for the self-assembly of "off-on-off" fluorescent sensors for pH windows," *Chemistry—A European Journal*, 12(3):921-930, 2006.

Extended European Search Report issued in European Application No. 17205562.6, dated May 9, 2018.

Extended European Search Report issued in European Application No. 16204435.8, dated Apr. 10, 2017.

Extended European Search Report issued in European Patent Application No. 11 82 7074, dated Feb. 26, 2014.

Ghosh et al., "Simultaneous and reversible functionalization of copolymers for biological applications," *Macromolecules*, 39:5595-5597, 2006.

Giacomelli et al., "Specific interactions improve the loading capacity of block copolymer micelles in aqueous media," *Langmuir*, 23:6947-6955, 2007.

Gijs et al., "Thiol chemistry on well-defined synthetic polypeptides," *Chem Comm.*, 24:3612-3614, 2009.

Griset et al., "Expansile nanoparticles: synthesis, characterization, and in vivo efficacy of an acid-responsive polymeric drug delivery system," *J Am Chem Soc.*, 131:2469-2471, 2009.

Han et al., "Fluorescent indicators for intracellular pH," *Chem Rev.*, 110(5):2709-28, 2010.

Heffernan et al., "Polyketal nanoparticles: a new pH-sensitive biodegradable drug delivery vehicle," *Bioconjugate Chem.*, 16:1340-1342, 2005.

Hu et al., "Synthesis and pH-dependent micellization of 2-(diisopropylamino)ethyl methacrylate based amphiphilic diblock copolymers via RAFT polymerization," *Polymer*, 48:3437-3443, 2007.

Izumi et al., "Cellular pH regulators: potentially promising molecular targets for cancer chemotherapy," *Cancer Treat Rev.*, 29(6):541-9, 2003.

Jung et al., "pH-sensitive polymer nanospheres for use as a potential drug delivery vehicle," *Biomacromolecules*, 8:3401-7, 2007.

Kato et al., "Polymerization of methyl methacrylate with the carbon tetrachloride/dichlorotris-(triphenylphosphine)ruthedum(II)/methylaluminum bis(2,6-di-tert-butylphenoxide) initiating system: possibility of living radical polymerization," *Macromolecules*, 28:1721-1723, 1995.

Khemtong et al., "In vivo off-resonance saturation magnetic resonance imaging of $\alpha_v\beta_3$-targeted superparamagnetic nanoparticles," *Cancer Res.*, 69:1651-1658, 2009.

Kim et al., "Doxorubicin loaded pH-sensitive micelle: antitumoral efficacy against ovarian A2780/DOXR tumor," *Pharm Res.*, 25:2074-82, 2008.

Kim et al., "Multicenter phase II trial of Genexol-PM, a novel Cremophor-free, polymeric micelle formulation of paclitaxel, with cisplatin in patients with advanced non-small-cell lung cancer," *Ann Oncol.*, 18(12):2009-14, 2007.

Kobayashi et al., "New strategies for fluorescent probe design in medical diagnostic imaging," *Chem Rev.*, 110(5):2620-40, 2010.

(56) References Cited

OTHER PUBLICATIONS

Kobayashi et al., "Target-cancer-cell-specific activatable fluorescence imaging probes: rational design and in vivo applications," *Acc Chem Res.*, 44(2):83-90, 2011.
Lakowicz, "Chapter 13. Energy Transfer," *Principles of Fluorescence Spectroscopy*, 3$^{rd}$ ed., New York City: Springer, 2006. 443-475. Print.
Lee et al., "Activatable imaging probes with amplified fluorescent signals," *Chem Commun.*, 36:4250-60, 2008.
Lee et al., "Doxorubicin loaded pH-sensitive polymeric micelles for reversal of resistant MCF-7 tumor," *J Control Release*, 103:405-18, 2005.
Lee et al., "Poly(L-histidine)-PEG block copolymer micelles and pH-induced destabilization," *J Control Release*, 90:363-74, 2003.
Li et al., "pH-activated near-infrared fluorescence nanoprobe imaging tumors by sensing the acidic microenvironment," *Adv Funct Mater.*, 20:2222-2230, 2010.
Licciardi et al., "Synthesis of novel folic acid-functionalized biocompatible block copolymers by atom transfer radical polymerization for gene delivery and encapsulation of hydrophobic drugs," *Biomacromolecules*, 6:1085-1096, 2005.
Lopalco et al., "Catch and release microwave mediated synthesis of cyanine dyes," *Org Biomol Chem.*, 7:856-859, 2009.
Lovell et al., "Activatable photosensitizers for imaging and therapy," *Chem Rev.*, 110(5):2839-57, 2010.
Ma et al., "Well-defined biocompatible block copolymers via atom transfer radical polymerization of 2-methacryloyloxyethyl phosphorylcholine in protic media," *Macromolecules*, 36(10):3475-3484, 2003.
Marconescu, "Targeting nanoparticles to tumor vasculature," *PhD Thesis*, UT Southwestern Medical Center, Dallas, 2008.
Maxfield et al., "Endocytic recycling," *Nat Rev Mol Cell Biol.*, 5(2)121-32, 2004.
Mcallister et al., "Polymeric nanogels produced via inverse microemulsion polymerization as potential gene and antisense delivery agents," *J Am Chem Soc.*, 124:15198-15207, 2002.
Moad et al., "Living radical polymerization by the RAFT process," *Australian Journal of Chemistry*, 58(6):379-410, 2005.
Modi et al., "A DNA nanomachine that maps spatial and temporal pH changes inside living cells," *Nat Nanotech.*, 4:325-330, 2009.
Nakanishi et al., "Development of the polymer micelle carrier system for doxorubicin," *J Control Release*, 74:295-302, 2001.
Nasongkla et al., "Multifunctional polymeric micelles as cancer-targeted, MRI-ultrasensitive drug delivery systems," *Nano Lett.*, 6:2427-2430, 2006.
Nishi et al., "The vacuolar (H+)-ATPases—nature's most versatile proton pumps," *Nat Rev Mol Cell Biol.*, 3(2):94-103, 2002.
Office Action issued in Australian Application No. 2011306076, dated May 1, 2014.
Office Action issued in Australian Application No. 2011306079, dated Feb. 27, 2015.
Office Action issued in Australian Application No. 2015203892, dated Aug. 3, 2015.
Office Action issued in Australian Application No. 2016203456, dated Feb. 7, 2017.
Office Action issued in Canadian Application No. 2,811,692, dated Nov. 20, 2017.
Office Action issued in European Application No. 11827074.3, dated Jan. 8, 2015.
Office Action issued in European Application No. 11827074.3, dated Nov. 26, 2015.
Office Action issued in European Application No. 16204435.8, dated Jan. 30, 2018.
Office Action issued in Japanese Application No. 2013-530130, dated Jul. 8, 2015. (English translation of Japanese text).
Office Action issued in Japanese Application No. 2013-530130, dated May 16, 2016, and English language translation thereof.
Office Action issued in Japanese Application No. 2016-175152, dated Jul. 11, 2018, and English language translation thereof.
Office Action issued in Japanese Application No. 2016-175152, dated Sep. 6, 2017, and English language translation thereof.
Office Action issued in U.S. Appl. No. 13/825,518, dated Apr. 30, 2015.
Office Action issued in U.S. Appl. No. 13/825,518, dated Jan. 21, 2015.
Office Action issued in U.S. Appl. No. 13/825,518, dated Sep. 18, 2015.
Office Action issued in U.S. Appl. No. 15/072,522, dated May 26, 2016.
Office Action issued in U.S. Appl. No. 15/072,522, dated Oct. 13, 2016.
PCT International Preliminary Report on Patentability issued in International application No. PCT/US2011/001418, dated Apr. 4, 2013.
PCT International Preliminary Report on Patentability issued in International application No. PCT/US2011/047497, dated Apr. 4, 2013.
PCT International Preliminary Report on Patentability issued in International Application No. PCT/US2013/035050, dated Oct. 16, 2014.
PCT International Search Report and Written Opinion issued in International application No. PCT/US2011/001418, dated Dec. 2, 2011.
PCT International Search Report and Written Opinion issued in International application No. PCT/US2011/047497, dated Oct. 21, 2011.
PCT International Search Report and Written Opinion issued in International Application No. PCT/US2013/035050, dated Sep. 10, 2013.
Reinicke et al., "Develoment of beta-Lapachone prodrugs for therapy against human cancer cells with elevated NAD(P)H:Quinone Oxidoreductase 1 levels," *Clin Cancer Res.*, 11:3055-3064, 2005.
Seshadri et al., "The delivery of superoxide dismutase encapsulated in polyketal microparticles to rat myocardium and protection from myocardial ischemia-reperfusion injury," *Biomaterials*, 31:1372-1379, 2010.
Srikun et al., "A dendrimer-based platform for simultaneous dual fluorescence imaging of hydrogen peroxide and pH gradients produced in living cells," *Chemical Science*, 2:1156-1165, 2011.
Sun et al., "Bright fluorescent nanoparticles for developing potential optical imaging contrast agents," *Nanoscale*, 2:548-558, 2010.
Sutton et al., "Doxorubicin and beta-lapachone release and interaction with micellar core materials: experiment and modeling," *Exp Biol Med.*, 232(8):1090-9, 2007.
Sutton et al., "Functionalized micellar systems for cancer targeted drug delivery," *Pharmaceutical Research*, 24(6):1029-1049, 2007.
Sutton, "Chapter 5: Hydrophobic prodrug strategy for the creation of polymeric micelles with pHsensitive release of beta-lapachone," *pH Sensitive RNA and Drug Delivery Systems—Ph.D. Dissertation*, Case Western Reserve University, Cleveland, 2007. 174-206.
Sy et al., "Surface functionalization of polyketal microparticles with nitrilotriacetic acid-nickel complexes for efficient protein capture and delivery," *Biomaterials*, 31:4987-4994, 2010.
Tsarevsky et al., "'Green' atom transfer radical polymerization: from process design to preparation of well-defined environmentally friendly polymeric materials," *Chem. Rev.*, 107(6):2270-99, 2007.
Uchiyama et al., "Multiplexing sensory molecules map protons near micellar membranes," *Angew Chem Int Ed Engl.*, 47(25):4667-9, 2008.
Ueno et al., "Fluorescent probes for sensing and imaging," *Nat methods*, 8(8):642-5, 2011.
Urano et al., "Selective molecular imaging of viable cancer cells with pH-activatable fluorescence probes," *Nat Med.*, 15:104-109, 2009.
Vetvicka et al., "Biological evaluation of polymeric micelles with covalently bound doxorubicin," *Bioconjug Chem.*, 20:2090-2097, 2009.
Wang et al., "Controlled living radical polymerization—atom-transfer radical polymerization in the presence of transition-metal complexes," *J Am. Chem Soc.*, 117:5614-5615, 1995.
Webb et al., "Dysregulated pH: a perfect storm for cancer progression," *Nat Rev Cancer*, 11(9):671-7, 2011.

(56) References Cited

OTHER PUBLICATIONS

Ye et al., "Novel near-infrared fluorescent integrin-targeted DFO analogue," *Bioconjug Chem.*, 19:225-234, 2007.

Yezhelyev et al., "Proton-sponge coated quantum dots for siRNA delivery and intracellular imaging," *J Am Chem Soc.*, 130(28):9006-12, 2008.

Yu et al., "Overcoming endosomal barrier by amphotericin B-loaded dual pH-responsive PDMA-b-PDPA micelleplexes for siRNA delivery," *ACS Nano*, 5(11):9246-55, 2011.

Zhang et al., "Creating new fluorescent probes for cell biology," *Nat Rev Mol Cell Biol.*, 3(12):906-18, 2002.

Zhou et al., "Tunable, ultra-sensitive pH responsive nanoparticles targeting specific endocytic organelles in living cells," *Angew Chem Int Ed Engl.*, 50:6109-6114, 2011.

Office Action issued in Australian Application No. 2017272262, dated Nov. 30, 2018.

Office Action issued in U.S. Appl. No. 16/814,803, dated Aug. 5, 2020.

Office Action issued in U.S. Appl. No. 16/814,803, dated Nov. 12, 2020.

Office Action issued in U.S. Appl. No. 16/814,898, dated Jan. 14, 2021.

Vamvakaki et al., "Synthesis of controlled structure water-soluble deblock copolymers via oxyanionic polymerization," *Macromolecules*, 32:2088-2090, 1999.

PEO-*b*-(PR-*r*-TMR)

FIG. 14A-B

BLOCK COPOLYMER AND MICELLE COMPOSITIONS AND METHODS OF USE THEREOF

CROSS-REFERENCE TO RELATED APPLICATIONS

This application is a continuation of U.S. patent application Ser. No. 15/662,184, filed Jul. 27, 2017, which is a continuation of U.S. patent application Ser. No. 15/072,522, filed Mar. 17, 2016, now U.S. Pat. No. 9,751,970, which is a continuation of U.S. patent application Ser. No. 13/825,518, filed Oct. 8, 2013, now abandoned, which is a national phase application under 35 U.S.C. § 371 of International Application Number PCT/US2011/001418, filed Aug. 11, 2011, which claims the benefit under 35 U.S.C. § 119(e) of U.S. Provisional Application Ser. Nos. 61/471,054, filed Apr. 1, 2011, 61/470,441, filed Mar. 31, 2011, and 61/385,422, filed Sep. 22, 2010, the contents of each of which are incorporated herein by reference in their entirety.

STATEMENT REGARDING FEDERALLY SPONSORED RESEARCH OR DEVELOPMENT

This invention was made with government support under Grant Numbers CA129011, CA102792 and EB005394 awarded by the National Institutes of Health. The government has certain rights in the invention.

BACKGROUND OF THE INVENTION

Multifunctional nanoparticles have received attention in a wide range of applications such as biosensors, diagnostic nanoprobes and targeted drug delivery systems. These efforts have been driven to a large extent by the need to improve biological specificity with reduced side effects in diagnosis and therapy through the precise, spatiotemporal control of agent delivery in various physiological systems. In order to achieve this goal, efforts have been dedicated to develop stimuli-responsive nanoplatforms. Environmental stimuli that have been exploited for pinpointing the delivery efficiency include pH, temperature, enzymatic expression, redox reaction and light induction. Among these activating signals, pH trigger is one of the most extensively studied stimuli based on two types of pH differences: (a) pathological (e.g. tumor) vs. normal tissues and (b) acidic intracellular compartments.

For example, due to the unusual acidity of the tumor extracellular microenvironment ($pH_e \approx 6.5$), several $pH_e$-responsive nanosystems have been reported to increase the sensitivity of tumor imaging or the efficacy of therapy. However, for polymer micelle compositions that release drug by hydrolysis in acidic environments, it can take days for the release of the drug. In that time period, the body can excrete or break down the micelles.

To target the acidic endo-/lysosomal compartments, nanovectors with pH-cleavable linkers have been investigated to improve payload bioavailability. Furthermore, several smart nanovectors with pH-induced charge conversion have been designed to increase drug efficacy. Despite these advances, specific transport and activation of nanoparticles and their interactions with different endocytic organelles during endocytosis in living cells is not well understood. The endocytic system is comprised of a series of compartments that have distinctive roles in the sorting, processing and degradation of internalized cargo. Selective targeting of different endocytic compartments by pH-sensitive nanoparticles is particularly challenging due to the short nanoparticle residence times (<mins) and small pH differences in these compartments (e.g. <1 pH unit between early endosomes and lysosomes).

Angiogenesis, the formation of new blood vessels, plays an essential role in normal physiological processes such as development and wound repair. Pathological angiogenesis occurs in tumors as well as a range of non-neoplastic diseases (e.g. diabetic retinopathy, endometriosis). In cancer, the formation of new blood vessels from an existing vasculature network is necessary for sustained tumor growth and exchange of nutrients and metabolic wastes. In the tumor microenvironment model of carcinogenesis, angiogenesis represents the last critical step to overcome the ischemia barrier. Acquisition of the angiogenic phenotype results in rapid tumor expansion, as well as facilitation of local invasion and cancer metastasis.

Tumor angiogenesis is a complex biological process that is orchestrated by a range of angiogenic factors. Initially, stressed tumor cells (e.g. under hypoxia) secrete growth factors and chemokines (e.g. VEGF-A) that stimulate quiescent vascular endothelium from adjacent host vessels to sprout new capillaries. These growth factors activate or upregulate the expression of integrins (e.g. $\alpha_v\beta_3$, $\Box \alpha_v\beta_5$) on blood vessels, which promote endothelial cell migration and survival in the creation of new vessel sprouts. Mechanistic understanding of tumor angiogenesis has propelled the rapid development of a variety of antiangiogenesis agents. Bevacizumab (Avastin®, Genentech) is a humanized anti-VEGF antibody that inhibits VEGF binding to and signaling through VEGFR1 and VEGFR2 receptors that are overexpressed on angiogenic endothelial cells. It is clinically approved in combination with cytotoxic chemotherapy for the treatment of colorectal cancer, non-small cell lung cancer, and breast cancer. Sunitinib (Sutent®, Pfizer) and sorafenib (Nexavar®, Bayer Pharm. Corp.) are small molecule inhibitors of multiple receptor tyrosine kinases including the VEGF receptors. They have been approved by the FDA for the treatment of renal cell carcinoma, GI stromal tumors (sunitinib), and unresectable liver cancer (sorafenib). A variety of other targeted agents are currently in late stage clinical trials (e.g. Vitaxin and Cilengitide, which target $\alpha_v\beta_3$ integrin, are in phase II/III clinical trials for treatment of metastatic melanoma and prostate cancer).

Angiogenesis imaging holds considerable promise for early detection of cancer, as well as post-therapy assessment of many new molecular-targeted antiangiogenic therapies. Two main strategies, functional and targeted imaging, are currently employed in angiogenesis imaging. Functional imaging strategy measures the blood flow, tumor blood volume and vascular permeability of solid tumors. These imaging techniques include Doppler ultrasound, dynamic contrast-enhanced CT or MM. The major advantages are that they can be easily adapted and have already been clinically implemented to monitor the efficacy of antiangiogenic drugs. The major drawback is that these methods are not very specific toward tumor angiogenesis. Recently, targeted imaging strategy is under intensive investigation with potential advantage of more precise characterization of the state of endothelium in a tumor. Among key angiogenesis targets are VEGF and its receptors, integrins (e.g. $\alpha_v\beta_3$ and $\alpha_v\beta_5$), and matrix metalloproteases. Various imaging modalities, such as PET, MRI, optical imaging, ultrasound, are being investigated with different degrees of success.

For cancer molecular imaging applications, achieving high contrast sensitivity and specificity remains a formidable challenge. Currently, most conventional imaging probes utilize an always ON design of contrast probes and the contrast sensitivity arises from the difference in tissue accumulation of the imaging payloads. Low tissue concentrations of intended biomarkers, lack of an amplification strategy to increase signal output, and high background signals are several major limiting factors. For small molecular radiotracers (e.g. $^{64}$Cu-labeled cRGD), although the detection sensitivity is very high (e.g. $<10^{-12}$ M), the contrast sensitivity is limited by their relatively low binding affinity to the targeted receptors and insufficient accumulation of imaging payloads in the targeted tissues. Monoclonal antibodies (mAbs) have shown superb affinity and specificity to a variety of cancer cell surface markers. However, radiolabeled or fluorescently labeled mAbs are limited in molecular imaging applications due to their slow clearance times and persistent high background signals in blood. In many conventional contrast agents, the contrast sensitivity is intrinsically limited by the relatively low tissue concentrations of cancer biomarkers on one hand, and high non-specific background signals from the always ON nanoprobes on the other.

What is needed are improved pH-responsive micelle compositions for therapeutic and diagnostic applications, in particular compositions having one or more of: increased imaging and/or drug payloads, prolonged blood circulation times, high contrast sensitivity and specificity, rapid delivery of drug at the target site, and responsiveness within specific narrow pH ranges (e.g. for targeting of tumors or specific organelles).

SUMMARY OF THE INVENTION

In one aspect of the invention is a block copolymer comprising a hydrophilic polymer segment and a hydrophobic polymer segment, wherein the hydrophilic polymer segment comprises a polymer selected from the group consisting of: poly(ethylene oxide) (PEO), poly(methacrylate phosphatidyl choline) (MPC), and polyvinylpyrrolidone (PVP), wherein the hydrophobic polymer segment comprises

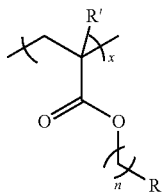

wherein R' is —H or —CH$_3$, wherein R is —NR$^1$R$^2$, wherein R$^1$ and R$^2$ are alkyl groups, wherein R$^1$ and R$^2$ are the same or different, wherein R$^1$ and R$^2$ together have from 5 to 16 carbons, wherein R$^1$ and R$^2$ may optionally join to form a ring, wherein n is 1 to about 10, wherein x is about 20 to about 200 in total, and wherein the block copolymer optionally comprises a labeling moiety. In some embodiments, the hydrophilic polymer segment comprises PEO. In some embodiments, n is 1 to 4. In some embodiments, n is 2. In some embodiments, R' is —CH$_3$. In some embodiments, R' is —H. In some embodiments, x is about 40 to about 100 in total. In some embodiments, x is about 50 to about 100 in total. In some embodiments, x is about 40 to about 80 in total. In some embodiments, x is about 60 to about 80 in total. In some embodiments, x is about 70 in total. In some embodiments, R$^1$ and R$^2$ are each straight or branched alkyl. In some embodiments, R$^1$ and R$^2$ join to form a ring. In some embodiments, R$^1$ and R$^2$ are the same. In some embodiments, R$^1$ and R$^2$ are different. In some embodiments, R$^1$ and R$^2$ each have 3 to 8 carbons. In some embodiments, R$^1$ and R$^2$ together form a ring having 5 to 10 carbons. In some embodiments, R$^1$ and R$^2$ are propyl. In some embodiments, propyl is iso-propyl. In some embodiments, R$^1$ and R$^2$ are butyl. In some embodiments, butyl is n-butyl. In some embodiments, le and R$^2$ together are —(CH$_2$)$_5$—. In some embodiments, R$^1$ and R$^2$ together are —(CH$_2$)$_6$—. In some embodiments, the block copolymer comprises a compound of Formula I:

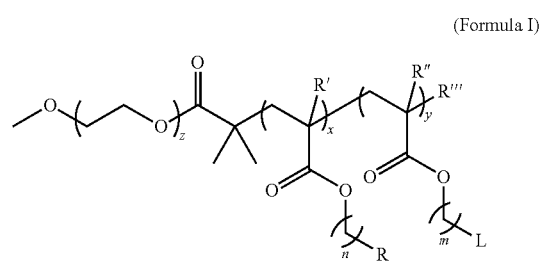

(Formula I)

wherein L is a labeling moiety, wherein y is 0 to about 6, wherein R" is —H or —CH$_3$; wherein m is 1 to about 10; wherein z is such that the PEO is about 2 kD to about 20 kD in size, wherein R''' is any suitable moiety, and wherein the following portion of the structure:

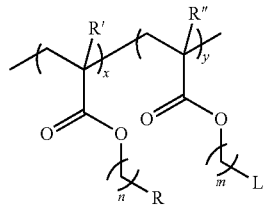

may be arranged in any order. In some embodiments, R" is —CH$_3$. In some embodiments, R" is —H. In some embodiments, m is 1 to 4. In some embodiments, m is 2. In some embodiments, the PEO is about 2 kD to about 10 kD in size. In some embodiments, the PEO is about 4 kD to about 6 kD in size. In some embodiments, the PEO is about 5 kD in size. In some embodiments, z is about 114. In some embodiments, y is 0. In some embodiments, y is 1 to 6. In some embodiments, y is about 3. In some embodiments, L is a fluorescent label. In some embodiments, the fluorescent label is tetramethyl rhodamine (TMR). In some embodiments, L is a near-infrared (NIR) label. In some embodiments, the NIR label is cypate. In some embodiments, the NIR label is a cypate analog. In some embodiments, R''' is an end group resulting from a polymerization reaction. In some embodiments, R''' is Br. In some embodiments, R''' is thiolate. In some embodiments, R''' is a thioester. In some embodiments, the following portion of the structure:

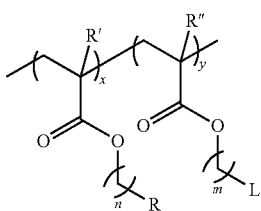

is randomized. In some embodiments, the block copolymer forms a pH-sensitive micelle.

In another aspect of the invention is a composition comprising a pH-sensitive micelle, wherein the pH-sensitive micelle comprises a block copolymer as described herein. It is to be understood that any of the block copolymers described herein may be utilized in making a pH-sensitive micelle. In some embodiments, the micelle has a size of about 10 to about 200 nm. In some embodiments, the micelle has a size of about 20 to about 100 nm. In some embodiments, the micelle has a size of about 30 to about 50 nm. In some embodiments, the micelle has a pH transition range of less than about 1 pH unit. In some embodiments, the micelle has a pH transition range of less than about 0.5 pH unit. In some embodiments, the micelle has a pH transition range of less than about 0.25 pH unit. In some embodiments, the micelle has a pH transition value of about 5 to about 8. In some embodiments, the micelle has a pH transition value of about 5 to about 6. In some embodiments, the micelle has a pH transition value of about 6 to about 7. In some embodiments, the micelle has a pH transition value of about 7 to about 8. In some embodiments, the micelle has a pH transition value of about 6.3 to about 6.9. In some embodiments, the micelle has a pH transition value of about 5.0 to about 6.2. In some embodiments, the micelle has a pH transition value of about 5.9 to about 6.2. In some embodiments, the micelle has a pH transition value of about 5.0 to about 5.5. In some embodiments, the micelle further comprises a targeting moiety. In some embodiments, the targeting moiety binds to VEGFR2. In some embodiments, the targeting moiety is a Fab' fragment of RAFL-1 mAb. In some embodiments, the targeting moiety binds to 43 integrin. In some embodiments, the targeting moiety is cRGDfK. In some embodiments, the targeting moiety binds to an angiogenesis biomarker. In some embodiments, the angiogenesis biomarker is VEGF-VEGFR complex or endoglin. In some embodiments, the composition further comprises a drug encapsulated within the micelle. In some embodiments, the drug is hydrophobic. In some embodiments, the drug has a log p of about 2 to about 8. In some embodiments, the drug is a chemotherapeutic agent. In some embodiments, the drug is doxorubicin. In some embodiments, the drug is beta-lapachone. In some embodiments, the drug is paclitaxel.

In another aspect of the invention is a method for treating cancer in an individual in need thereof, comprising administration of an effective amount of a pH-sensitive micelle composition comprising a chemotherapeutic agent as described herein. In some embodiments, the cancer comprises a solid tumor.

In another aspect of the invention is a method for imaging a tumor in an individual, comprising a) administering a pH-sensitive micelle composition as described herein to the individual, wherein the block copolymer comprises a labeling moiety, and b) determining the distribution of the block copolymer in its disassociated form. In some embodiments, the method is used to diagnose a tumor in the individual. In some embodiments, the method is used to monitor a tumor in the individual.

In another aspect of the invention is a method for delivery of a drug to early endosomes, comprising administration of a pH-sensitive micelle composition comprising a drug as described herein to an individual in need thereof, wherein the micelle has a pH transition value of about 5.9 to about 6.5.

In another aspect of the invention is a method for delivery of a drug to late endosomes or lysosomes, comprising administration of a pH-sensitive micelle composition comprising a drug as described herein to an individual in need thereof, wherein the micelle has a pH transition value of about 5.0 to about 5.5. In some embodiments, the drug is a lysosomal storage disease drug.

In another aspect of the invention is a method for imaging early endosomal activity in an individual, comprising a) administration of a pH sensitive micelle composition as described herein to the individual, wherein the block copolymer comprises a labeling moiety, and wherein the micelle has a pH transition value of about 5.9 to about 6.5, and b) determining the distribution of the block copolymer in its disassociated form.

In another aspect of the invention is a method for imaging late endosomal or lysosomal activity in an individual, comprising a) administration of a pH sensitive micelle composition as described herein to the individual, wherein the block copolymer comprises a labeling moiety, and wherein the micelle has a pH transition value of about 5.0 to about 5.5, and b) determining the distribution of the block copolymer in its disassociated form.

In another aspect of the invention is a compound of the formula:

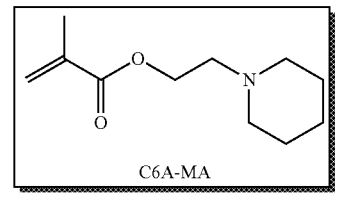

In another aspect of the invention is a polymer of the compound C6A-MA.

In another aspect of the invention is a compound of the formula:

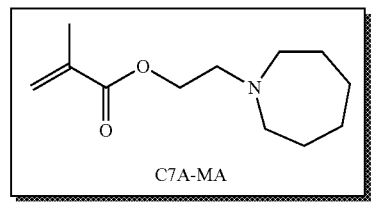

In another aspect of the invention is a polymer of the compound C7A-MA.

In another aspect of the invention is a compound of the formula:

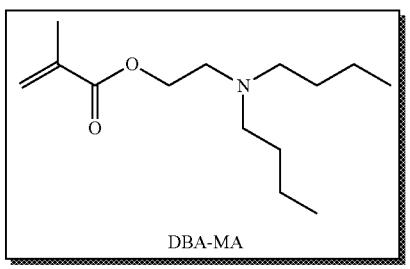

In another aspect of the invention is a polymer of the compound DBA-MA.

BRIEF DESCRIPTION OF THE FIGURES

FIG. 5A shows signal to noise ratios (SNRs) of 3 inside H2009 cells and medium over time. FIG. 5B shows a comparison of SNR between H2009 cells and medium before and after the addition of HCl. A large contrast ($SNR_{Cell}/SNR_{Med}$=31 at 60 min) was observed before HCl addition and the trend is reversed ($SNR_{Cell}/SNR_{Med}$=0.74) after HCl. P-values were calculated using the Student's t-test.

DETAILED DESCRIPTION OF THE INVENTION

The present invention provides block copolymers and micelle compositions comprising one or more of said block copolymers that are useful in one or more therapeutic and/or diagnostic applications, such as treatment of cancer, cardiovascular disease, inflammation, an autophagy-related disease, or lysosomal storage disease, tumor imaging, and/or imaging of intracellular organelles such as early endosomes, late endosomes and lysosomes. The invention further provides methods for using the micelle compositions in such therapeutic and diagnostic applications.

The block copolymers of the invention comprise a hydrophilic polymer segment and a hydrophobic polymer segment, wherein the hydrophobic polymer segment comprises an ionizable amine group to render pH sensitivity. The block copolymers form pH-activatable micellar (pHAM) nanoparticles based on the supramolecular self-assembly of these ionizable block copolymers (see e.g. FIG. 1C). For example, FIG. 1C illustrates the design principle of a non-limiting example of a micelle of the invention. At higher pH, the block copolymers assemble into micelles, whereas at lower pH, ionization of the amine group in the hydrophobic polymer segment results in dissociation of the micelle. Without wishing to be bound by theory, micelle formation and its thermodynamic stability are driven by the delicate balance between the hydrophobic and hydrophilic segments. The ionizable groups may act as tunable hydrophilic/hydrophobic blocks at different pH values, which may directly affect the dynamic self-assembly of micelles. Without wishing to be bound by theory, micellization may sharpen the ionization transition of the amines in the hydrophobic polymer segment, rendering fast and ultra-sensitive pH response. Different block copolymers may be selected to provide micelles having different transition pH values within physiological range, in order to achieve selective activation within various environments, such as tumors (e.g. the extracellular environment of tumors), or within specific endocytic compartments such as early or late endosomes or lysosomes.

Figure 15:
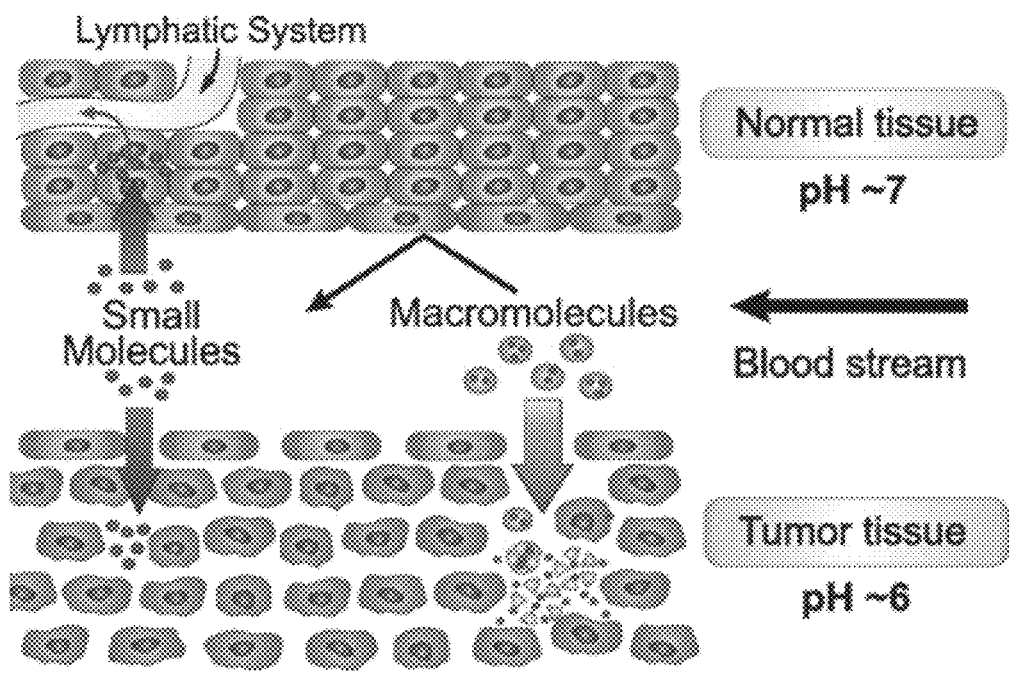
FIG. 15 illustrates selective targeting of drug delivery to a tumor by a larger macromolecule such as a micelle of the invention.

For therapeutic applications, a drug may be incorporated into the interior of the micelles. Specific pH conditions (e.g. acidic pH present in tumors and endocytic compartments) may lead to rapid protonation and dissociation of micelles into unimers, thereby releasing the drug. In some embodiments, the micelle provides stable drug encapsulation at physiological pH (pH 7.4), but can quickly release the drug in acidic environments. The micelles of the invention may provide one or more advantages in therapeutic applications, such as: (1) disassociation of the micelle (and rapid release of drug) within a short amount of time (e.g. within minutes) under certain pH environments (e.g. acidic environments), as opposed to hours or days for previous micelle compositions; (2) encapsulation of a high percentage of drug; (3) selective targeting of drug delivery to the desired site (e.g. tumor or lysosome), which may enhance drug efficacy and reduce toxicity to healthy cells (see e.g. FIG. 15); (4) prolonged blood circulation times; (5) responsiveness within specific narrow pH ranges (e.g. for targeting of specific organelles), and (6) image-guided therapy, where imaging signals can be a predictive factor for the therapeutic efficacy for the treatment.

Figure 12:
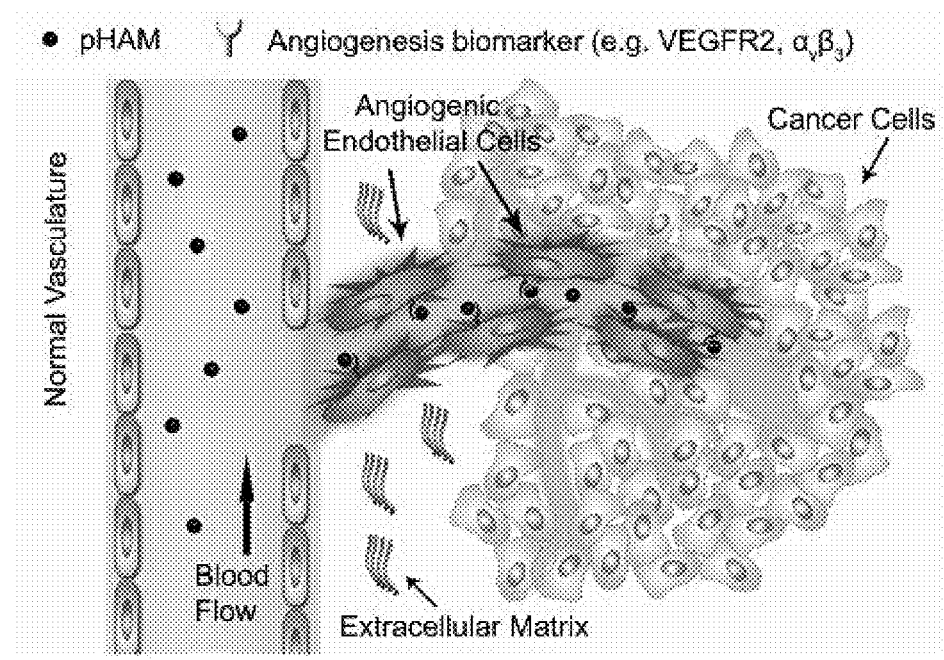
FIG. 12 illustrates an example of pH-activatable (pHAM) nanoprobes for imaging of angiogenesis biomarkers (e.g. VEGFR2, $\alpha_v\beta_3$) in vascularized tumors. These nanoprobes will stay "silent" (or OFF state) during blood circulation, but can be turned ON by pH activation after receptor-mediated endocytosis in angiogenic tumor endothelial cells.
Figure 13:
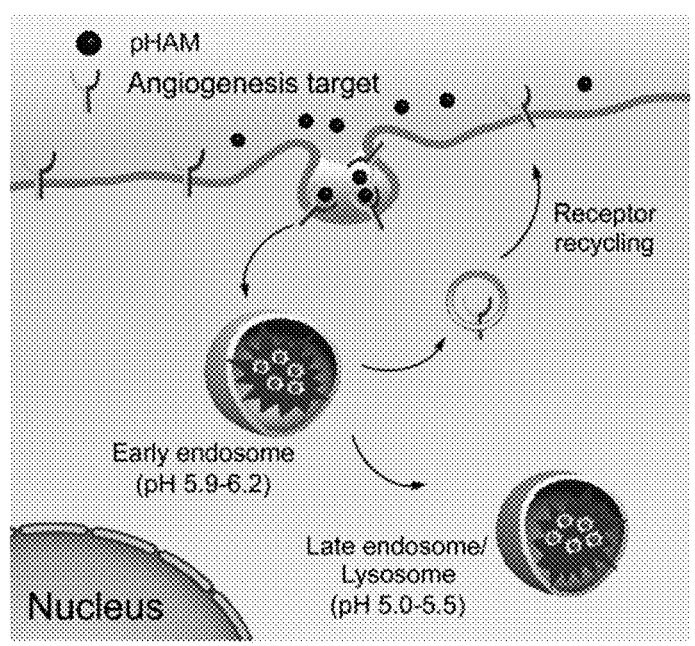
FIG. 13 illustrates an example of intracellular activation mechanism for a vascular targeted pHAM inside acidic intracellular organelles (i.e. endosomes/lysosomes).

For diagnostic applications, a labeling moiety may be conjugated to the block copolymer. In some embodiments, the label (e.g. a fluorescent label) is sequestered inside the micelle when the pH favors micelle formation, and sequestration results in a decrease in label signal (e.g. via fluorescence quenching, see e.g. FIG. 1C). Specific pH conditions (e.g. acidic pH present in tumors and endocytic compartments) may lead to rapid protonation and dissociation of micelles into unimers, thereby exposing the label, and increasing the label signal (e.g. increasing fluorescence emission). The micelles of the invention may provide one or more advantages in diagnostic applications, such as: (1) disassociation of the micelle (and rapid increase in label signal) within a short amount of time (e.g. within minutes) under certain pH environments (e.g. acidic environments), as opposed to hours or days for previous micelle compositions; (2) increased imaging payloads; (3) selective targeting of label to the desired site (e.g. tumor or particular endocytic compartment); (4) prolonged blood circulation times; (5) responsiveness within specific narrow pH ranges (e.g. for targeting of specific organelles); and (6) high contrast sensitivity and specificity. For example, the micelles may stay silent (or in the OFF state) with minimum background signals under normal physiological conditions (e.g. blood circulation), but imaging signals can be greatly amplified when the micelles reach their intended molecular targets in vivo (e.g. extracellular tumor environment or cellular organelle). As a non-limiting example, upon specific targeting to angiogenic biomarkers (e.g. $\alpha_v\beta_3$), micelle nanoprobes can be turned ON by pH activation inside endosomes/lysosomes after receptor-mediated endocytosis. FIG. 12 illustrates an example of pH-activatable (pHAM) nanoprobes for imaging of angiogenesis biomarkers (e.g. VEGFR2, $\alpha_v\beta_3$) in vascularized tumors. These nanoprobes will stay "silent" (or OFF state) during blood circulation, but can be turned ON by pH activation after receptor-mediated endocytosis in angiogenic tumor endothelial cells. FIG. 13 illustrates the intracellular activation mechanism for a vascular targeted pHAM inside acidic intracellular organelles (i.e. endosomes/lysosomes).

Definitions

As used herein, "alkyl" indicates any saturated hydrocarbon moiety, including, for example, straight chain, branched chain, or cyclic (including fused and spiro bicyclic and polycyclic) saturated hydrocarbon moieties which may optionally be substituted with one or more additional saturated hydrocarbon moieties.

As used herein, "pH-sensitive micelle", "pH-activatable micelle" and "pH-activatable micellar (pHAM) nanoparticle" are used interchangeably herein to indicate a micelle comprising one or more block copolymers, which disassociates depending on the pH (e.g. above or below a certain pH). As a non-limiting example, at a certain pH, the block copolymer is substantially in micellar form. As the pH changes (e.g. decreases), the micelles begin to disassociate, and as the pH further changes (e.g. further decreases), the block copolymer is present substantially in disassociated (non-micellar) form.

A "nanoprobe" is used herein to indicate a pH-sensitive micelle which comprises an imaging labeling moiety.

Figure 14:
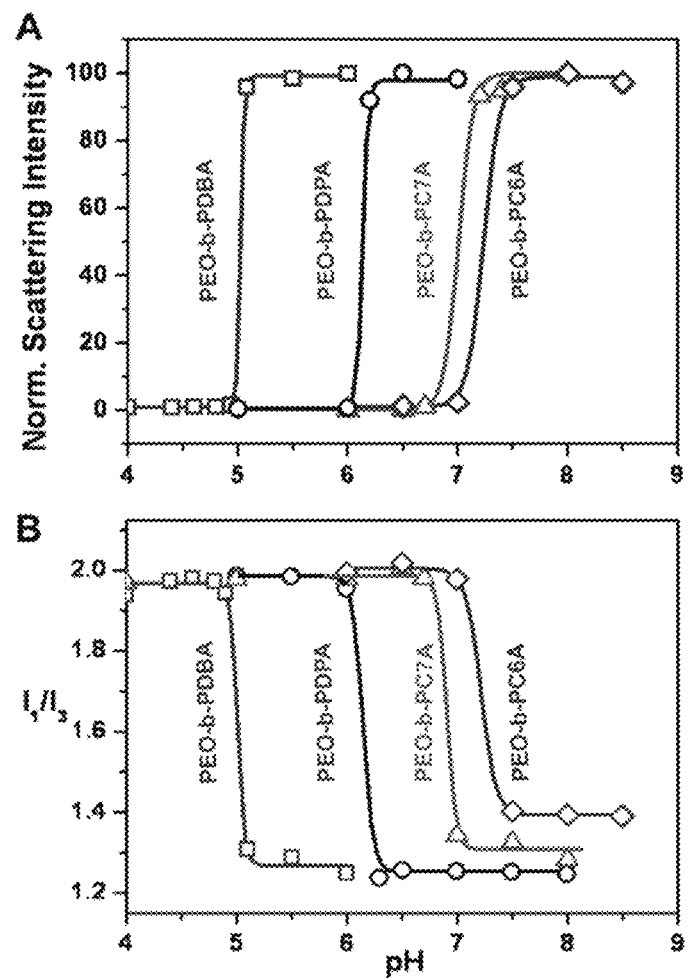
FIGS. 14A and 14B show pH-dependent micellization behaviors ((14A) normalized light scattering intensity and (14B) pyrene $I_1/I_3$ emission ratio as a function of pH) from 4 different PEG-b-PR copolymers having a concentration at 0.1 mg/ml.

As used herein, "pH transition range" indicates the pH range over which the micelles disassociate. In some embodiments, the pH transition range is the pH response sharpness. An example of determining pH response sharpness is described in Example 2 below. Briefly, the fluorescence intensity versus pH is measured for a block copolymer which comprises a fluorescent label that is sequestered within the micelle (quenching fluorescence) when the block copolymer is in micellar form (see e.g. FIG. 1C). As the pH changes (e.g. decreases), the micelle disassociates, exposing the fluorescent label and resulting in fluorescence emission. Normalized fluorescence intensity (NFI) vs. pH curves permit quantitative assessment of the pH responsive properties of the micelle. NFI is calculated as the ratio of $[F-F_{min}]/[F_{max}-F_{min}]$, where F is the fluorescence intensity of the micelle at any given pH, and $F_{max}$ and $F_{min}$ are the maximal and minimal fluorescence intensities at the ON/OFF states, respectively. pH response sharpness is $\Delta pH_{10-90\%}$, the pH range in which the NFI value varies from 10% to 90%. For label-free copolymers, dynamic light scattering (DLS) or an external fluorophore (e.g. pyrene) can be used to characterize the pH-dependent micellization behaviors. For example, FIG. 14A shows the normalized light scattering intensity of several PEO-b-PR copolymers at 0.1 mg/mL concentration as a function of pH. At different pH values, dramatic increase of light scattering intensity was observed due to the formation of micelle nanoparticles from unimers in solution. The hydrodynamic diameters of the resulting micelles were measured at 40-50 nm. The light scattering data was further supported by examining the $I_1/I_3$ ratios (at 372-374 and 382-384 nm, respectively) of pyrene emissions ($\lambda_{ex}$=339 nm) (FIG. 14B). $I_1/I_3$ ratio reflects the polarity of the pyrene environment where a partition of pyrene in the micelle core leads to decreased $I_1/I_3$ values.

As used herein, "pH transition value" ($pH_t$) indicates the pH at which half of the micelles are disassociated. An example of determining pH transition value is described in Example 2 below. Briefly, for a block copolymer which comprises a fluorescent label that is sequestered within the micelle (quenching fluorescence) when the block copolymer is in micellar form, the pH transition value is the pH at which the fluorescence emission measured is $0.5 \times (F_{max} + F_{min})$, where $F_{max}$ and $F_{min}$ are the maximal and minimal fluorescence intensities at the ON/OFF states, respectively. For label-free copolymers, dynamic light scattering (DLS) or an external fluorophore (e.g. pyrene) can be used to characterize the pH-dependent micellization behaviors. For example, FIG. 14A shows the normalized light scattering intensity of several PEO-b-PR copolymers at 0.1 mg/mL concentration as a function of pH. At different pH values, dramatic increase of light scattering intensity was observed due to the formation of micelle nanoparticles from unimers in solution. The hydrodynamic diameters of the resulting micelles were measured at 40-50 nm. The light scattering data was further supported by examining the $I_1/I_3$ ratios (at 372-374 and 382-384 nm, respectively) of pyrene emissions ($\lambda_{ex}=339$ nm) (FIG. 14B). $I_1/I_3$ ratio reflects the polarity of the pyrene environment where a partition of pyrene in the micelle core leads to decreased $I_1/I_3$ values. Both light scattering and pyrene experiments yielded similar pH transition values. The $pH_t$ values were 5.0, 6.2, 7.0, and 7.2 for PEO-b-PDBA, PEO-b-PDPA, PEO-b-PC7A, PEO-b-PC6A, respectively.

As used herein, the term "treating" refers to a clinical intervention designed to alter the natural course of clinical pathology of the disease or disorder being treated (e.g., cancer). Desirable effects of treatment include, for example, ameliorating or palliating the disease state, slowing or reversing the progression of the disorder, remission, or improved prognosis.

As used herein, the term "effective amount" refers to an amount effective, at dosages and for periods of time necessary, to achieve the desired therapeutic, prophylactic, or diagnostic result. An effective amount can be provided in one or more administrations.

As used herein, "individual" indicates an animal, preferably a mammal, including humans, primates, laboratory animals (e.g. rats, mice, etc.), farm animals (e.g. cows, sheep, goats, pigs, etc.), pets (e.g. dogs, cats, etc.), and sport animals (e.g. horses, etc.). In some embodiments, an individual is a human.

Reference to "about" a value or parameter herein also includes (and describes) embodiments that are directed to that value or parameter per se.

As used herein and in the appended claims, the singular forms "a," "an," and "the" include plural reference unless the context clearly indicates otherwise.

It is understood that all aspects and embodiments of the invention described herein include "comprising," "consisting," and "consisting essentially of" aspects and embodiments. It is to be understood that methods or compositions "consisting essentially of" the recited elements include only the specified steps or materials and those that do not materially affect the basic and novel characteristics of those methods and compositions.

It is to be understood that any of the compositions described herein may be used in any of the methods as described herein, unless context clearly indicates otherwise.

Block Co-Polymer Compounds

Novel block copolymers are provided herein, comprising a hydrophilic polymer segment and a hydrophobic polymer segment, wherein the hydrophilic polymer segment comprises a polymer selected from the group consisting of: poly(ethylene oxide) (PEO), poly(methacrylate phosphatidyl choline) (MPC), and polyvinylpyrrolidone (PVP), wherein the hydrophobic polymer segment comprises

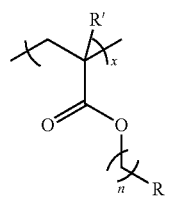

wherein R' is —H or —CH$_3$, wherein R is —NR$^1$R$^2$, wherein R$^1$ and R$^2$ are alkyl groups, wherein R$^1$ and R$^2$ are the same or different, wherein R$^1$ and R$^2$ together have from 5 to 16 carbons, wherein R$^1$ and R$^2$ may optionally join to form a ring, wherein n is 1 to about 10, wherein x is about 20 to about 200 in total, and wherein the block copolymer may further optionally comprise a labeling moiety. For example, x may be about 20 to about 200 as a continuous segment (i.e. a continuous segment of about 20 to about 200 monomer units), or other moieties (e.g. moieties comprising a label) may be interspersed between the monomer units, for example as described in more detail below.

Block copolymers of the invention include, for example, compounds of Formula I:

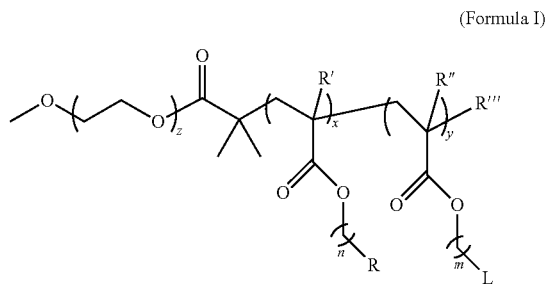

(Formula I)

wherein L is a labeling moiety, wherein y is 0 to about 6, wherein R" is —H or —CH$_3$; wherein m is 1 to about 10, wherein z is such that the PEO is about 2 kD to about 20 kD in size, wherein x, n, R, and R' are as defined above, wherein R'" is any suitable moiety, and wherein the following portion of the structure:

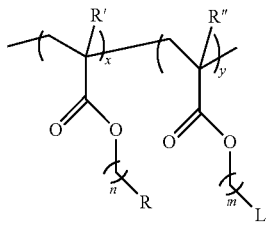

may be arranged in any order.

In some embodiments, R'" is an end group resulting from a polymerization reaction. For example, R'" may be —Br when atom transfer radical polymerization (ATRP) is used. It is to be understood that the chemical structures in FIGS. 1A, 2A, 2B, 8 and 9 may comprise a —Br as the end group resulting from the polymerization reaction. For example, R'" may be a sulfur-containing group such as thiolate or a thioester when reversible addition-fragmentation chain transfer (RAFT) is used. In some embodiments, R' is —Br. In some embodiments, R'" is thiolate. In some embodiments, R' is a thioester. The end group may optionally be further modified following polymerization with an appropriate moiety.

In some embodiments, the following portion of the structure:

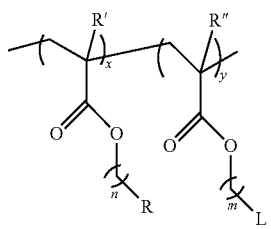

is randomized, i.e.:

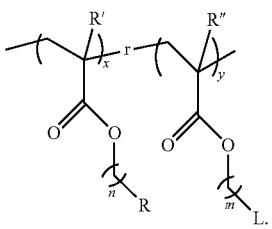

wherein r indicates a random ordering of the R containing moieties and the L containing moieties (i.e. the R containing moieties and the L containing moieties are randomly interspersed).

In some embodiments, the following portion of the structure:

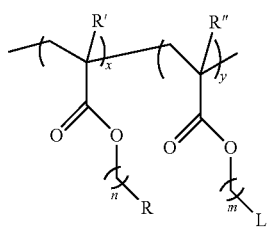

is arranged sequentially. For example, the R containing moieties may be present as a single block, with the L containing moieties present as a single block either preceding or following the R containing moieties. Other arrangements may also be utilized.

Hydrophilic Polymer Segment

In some embodiments, the hydrophilic polymer segment comprises poly(ethylene oxide) (PEO). In some embodiments, the hydrophilic polymer segment comprises poly (methacrylate phosphatidyl choline) (MPC). In some embodiments, the hydrophilic polymer segment comprises polyvinylpyrrolidone (PVP). In general, the PEO, MPC, or PVP polymer in the hydrophilic polymer segment is about 2 kD to about 20 kD in size. In some embodiments, the polymer is about 2 kD to about 10 kD in size. In some embodiments, the polymer is about 2 kD to about 5 kD in size. In some embodiments, the polymer is about 3 kD to about 8 kD in size. In some embodiments, the polymer is about 4 kD to about 6 kD in size. In some embodiments, the polymer is about 5 kD in size. In some embodiments, the polymer has about 100 to about 130 monomer units. In some embodiments, the polymer has about 110 to about 120 monomer units. In some embodiments, the polymer has about 114 monomer units. In some embodiments, the polydispersity index (PDI) of the polymer is less than about 1.2. In some embodiments, the polydispersity index (PDI) of the polymer is less than about 1.1.

Suitable PEO, MPC, and PVP polymers may be purchased (for example, PEO polymers may be purchased from Aldrich Sigma) or may be synthesized according to methods known in the art. In some embodiments, the hydrophilic polymer can be used as an initiator for polymerization of the hydrophobic monomers to form a block copolymer.

For example, MPC polymers (e.g. narrowly distributed MPC polymers) can be prepared by atom transfer radical polymerization (ATRP) with commercially available small molecule initiators such as ethyl 2-bromo-2-methylpropanoate (Sigma Aldrich). These resulting MPC polymers can be used as macromolecular ATRP initiators to further copolymerize with other monomers to form block polymers such as MPC-b-PDPA. PEO-b-PR block copolymers can be synthesized using atom transfer radical polymerization (ATRP) or reversible addition-fragmentation chain transfer (RAFT) methods (See e.g. Australian Journal of Chemistry Volume: 58 Issue: 6 Pages: 379-410 (2005); Progress in Polymer Science Volume: 32 Issue: 1 Pages: 93-146 (2007). ATRP or RAFT allows for living polymerization which can yield PEO-b-PR copolymers with narrow polydispersity (<1.1). Different metharylate or acrylate monomers can be used to produce PR segments with different pH sensitivity.

Hydrophobic Polymer Segment

The hydrophobic polymer segment comprises:

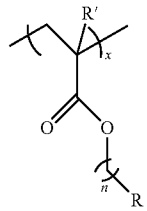

wherein R' is —H or —CH$_3$, wherein R is —NR$^1$R$^2$, wherein R$^1$ and R$^2$ are alkyl groups, wherein R$^1$ and R$^2$ are the same or different, wherein R$^1$ and R$^2$ together have from 5 to 16 carbons, wherein R$^1$ and R$^2$ may optionally join to form a ring, wherein n is 1 to about 10, and wherein x is about 20 to about 200 in total.

In some embodiments, n is 1 to 4. In some embodiments, n is 2. In various embodiments, n is 1, 2, 3, 4, 5, 6, 7, 8, 9, or 10.

In some embodiments, R' is —CH$_3$. In some embodiments, R' is —H.

In some embodiments, x is about 40 to about 100 in total. In some embodiments, x is about 50 to about 100 in total. In some embodiments, x is about 40 to about 70 in total. In some embodiments, x is about 60 to about 80 in total. In some embodiments, wherein x is about 70 in total.

In some embodiments, R$^1$ and R$^2$ together have from 5 to 14 carbons. In some embodiments, R$^1$ and R$^2$ together have from 5 to 12 carbons. In some embodiments, R$^1$ and R$^2$ together have from 5 to 10 carbons. In some embodiments, R$^1$ and R$^2$ together have from 5 to 8 carbons. In some embodiments, R$^1$ and R$^2$ together have from 6 to 12 carbons. In some embodiments, R$^1$ and R$^2$ together have from 6 to 10 carbons. In some embodiments, $R^1$ and $R^2$ together have from 6 to 8 carbons. In various embodiments, $R^1$ and $R^2$ together have 5, 6, 7, 8, 9, 10, 11, 12, 13, 14, 15, or 16 carbons. In some embodiments, $R^1$ and $R^2$ each have 3 to 8 carbons. In some embodiments, $R^1$ and/or $R^2$ comprise 3 carbons. In some embodiments, $R^1$ and/or $R^2$ comprise 4 carbons. In some embodiments, $R^1$ and/or $R^2$ comprise 5 carbons. In some embodiments, le and/or $R^2$ comprise 6 carbons. In some embodiments, $R^1$ and/or $R^2$ comprise 7 carbons. In some embodiments, $R^1$ and/or $R^2$ comprise 8 carbons. In some embodiments, $R^1$ and $R^2$ are the same. In some embodiments, $R^1$ and $R^2$ are different. In some embodiments, $R^1$ and $R^2$ are each independently straight or branched alkyl. In some embodiments, $R^1$ and $R^2$ are each straight alkyl. In some embodiments, $R^1$ and $R^2$ are each branched alkyl. Suitable alkyl groups for $R^1$ and $R^2$ include, for example, methyl, ethyl, propyl, butyl, pentyl, hexyl, heptyl, octyl, nonyl, decyl, undecyl, dodecyl, tridecyl, tetradecyl, and pentadecyl, including various possible skeletal isomers for each alkyl group such as n-, iso-, sec-, tert-, neo-, etc., provided the total number of carbons in R is from 5 to 16. In some embodiments, $R^1$ and $R^2$ are propyl. In some embodiments, propyl is iso-propyl. In some embodiments, propyl is n-propyl. In some embodiments, $R^1$ and $R^2$ are butyl. In some embodiments, butyl is n-butyl. In some embodiments, butyl is iso-butyl. In some embodiments, butyl is sec-butyl. In some embodiments, butyl is t-butyl. In some embodiments, le and $R^2$ join to form a ring. The ring may optionally be substituted with one or more alkyl groups, provided the total number of carbons in R is from 5 to 16. In some embodiments, $R^1$ and $R^2$ together form a ring having 5 to 10 carbons. In some embodiments, $R^1$ and $R^2$ together form a ring having 5 to 8 carbons. In some embodiments, $R^1$ and $R^2$ together form a ring having 5 to 7 carbons. In some embodiments, $R^1$ and $R^2$ together are —$(CH_2)_5$—. In some embodiments, $R^1$ and $R^2$ together are —$(CH_2)_6$—.

The hydrophobic polymer segment may be synthesized according to, e.g. Atom Transfer Radical Polymerization (ATRP) or reversible addition-fragmentation chain transfer (RAFT). An example of ATRP synthesis of a hydrophobic polymer segment may be found in Example 1. In some embodiments, the polydispersity index (PDI) for the hydrophobic polymer segment is less than about 1.2. In some embodiments, the polydispersity index (PDI) for the hydrophobic polymer segment is less than about 1.1.

Labeling Moiety

The block copolymer may optionally comprise one or more labeling moieties (e.g. 1, 2, 3, 4, 5, 6, or more). In some embodiments, the label is a fluorescent label. In some embodiments, the fluorescent label is tetramethyl rhodamine (TMR). In some embodiments, the label is a near-infrared (NIR) label. In some embodiments, the NIR label is cypate or a cypate analog.

When the block copolymer is a compound of Formula I, in some embodiments, R" is —$CH_3$. In some embodiments, R" is —H. In some embodiments, m is 1 to 4. In some embodiments, m is 2. In various embodiments, m is 1, 2, 3, 4, 5, 6, 7, 8, 9, or 10. In some embodiments, y is 0. In some embodiments, y is 1 to 6. In various embodiments, y is 1, 2, 3, 4, 5, or 6. In some embodiments, y is 3.

The labeling moiety may be conjugated to the copolymer directly or through a linker moiety. Methods known in the art may be used to conjugate the labeling moiety to, for example, the hydrophobic polymer. Examples of conjugation may be found in, for example, Examples 1 and 5 below.

The micelles of the invention may advantageously have high imaging payloads. In various embodiments, the micelles have at least about 500 dyes, at least about 1000, at least about 1500, at least about 2000, at least about 2400, at least about 3000 dyes per micelle. In comparison, typical immunofluorescent conjugates have 4 fluorophores per molecule, as a higher number will lead to dye quenching and may also modify binding epitopes.

Different labels may be preferred for the particular method of use. For example, tetramethylrhodamine may be used, e.g., for in vitro cell study on confocal imaging, while for animal imaging studies in vivo, NIR dyes may increase the tissue penetrations.

Exemplary Block Copolymers

Non-limiting examples of block copolymers of the invention include those described in the Examples below. Non-limiting examples of block copolymers of Formula I are provided in Table A.

TABLE A

Exemplary block copolymers

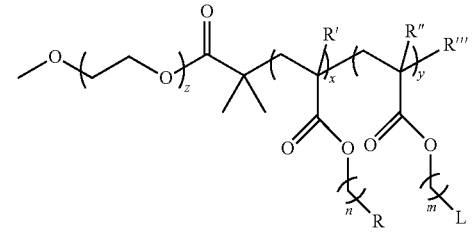

| Compound | R' | $R^1/R^2$ | n | z | R" | m | x | y | L | R''' |
|---|---|---|---|---|---|---|---|---|---|---|
| 3 (no label) | —$CH_3$ | iPr/iPr | 2 | 114 | — | — | 45 | 0 | None | Br |
| 4 (no label) | —$CH_3$ | nBu/nBu | 2 | 114 | — | — | 51 | 0 | None | Br |
| 6 (no label) | —$CH_3$ | —$(CH_2)_5$— | 2 | 114 | — | — | 45 | 0 | None | Br |
| 7 (no label) | —$CH_3$ | —$(CH_2)_6$— | 2 | 114 | — | — | 49 | 0 | None | Br |
| 3 (TMR label) | —$CH_3$ | iPr/iPr | 2 | 114 | —$CH_3$ | 2 | 70 | 3 | TMR | Br |
| 4 (TMR label) | —$CH_3$ | nBu/nBu | 2 | 114 | —$CH_3$ | 2 | 70 | 3 | TMR | Br |
| 6 (TMR label) | —$CH_3$ | —$(CH_2)_5$— | 2 | 114 | —$CH_3$ | 2 | 70 | 3 | TMR | Br |
| 7 (TMR label) | —$CH_3$ | —$(CH_2)_6$— | 2 | 114 | —$CH_3$ | 2 | 70 | 3 | TMR | Br |
| 3 (cypate label) | —$CH_3$ | iPr/iPr | 2 | 114 | —$CH_3$ | 2 | 70 | 3 | cypate | Br |
| 4 (cypate label) | —$CH_3$ | nBu/nBu | 2 | 114 | —$CH_3$ | 2 | 70 | 3 | cypate | Br |

TABLE A-continued

Exemplary block copolymers

| Compound | R' | R¹/R² | n | z | R" | m | x | y | L | R''' |
|---|---|---|---|---|---|---|---|---|---|---|
| 6 (cypate label) | —CH$_3$ | —(CH$_2$)$_5$— | 2 | 114 | —CH$_3$ | 2 | 70 | 3 | cypate | Br |
| 7 (cypate label) | —CH$_3$ | —(CH$_2$)$_6$— | 2 | 114 | —CH$_3$ | 2 | 70 | 3 | cypate | Br |

In Table A, the following portion of the structure:

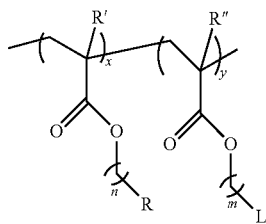

is randomized, i.e.:

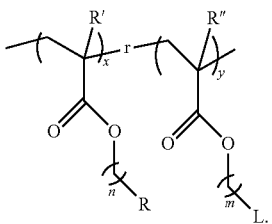

With regards to the compounds described herein, it is to be understood that polymerization reactions may result in a certain variability of polymer length, and that the numbers described herein indicating the number of monomer units within a particular polymer (e.g. x, y, z) may indicate an average number of monomer units. In some embodiments, a polymer segment described herein (e.g. the hydrophobic polymer segment, the hydrophilic polymer segment) has a polydispersity index (PDI) less than about 1.2. In some embodiments, the polydispersity index (PDI) for the polymer segment is less than about 1.1. In some embodiments, the polydispersity index (PDI) for the block copolymer is less than about 1.2. In some embodiments, the polydispersity index (PDI) for the block copolymer is less than about 1.1.

Micelle Compositions

One or more block copolymers (e.g. 2, 3, 4, 5, or more) described herein may be used to form a pH-sensitive micelle. In some embodiments, a composition comprises a single type of micelle. In some embodiments, two or more (e.g. 2, 3, 4, 5, or more) different types of micelles may be combined to form a mixed-micelle composition.

The pH-sensitive micelle compositions of the invention may advantageously have a narrow pH transition range, in contrast to other pH sensitive compositions in which the pH response is very broad (i.e. 2 pH units). In some embodiments, the micelles have a pH transition range of less than about 1 pH unit. In various embodiments, the micelles have a pH transition range of less than about 0.9, less than about 0.8, less than about 0.7, less than about 0.6, less than about 0.5, less than about 0.4, less than about 0.3, less than about 0.2, less than about 0.1 pH unit. In some embodiments, the micelles have a pH transition range of less than about 0.5 pH unit. In some embodiments, the micelles have a pH transition range of less than about 0.25 pH unit.

When the micelles comprise a fluorescent label, the narrow pH responsive properties of pHAM may improve the efficiency of fluorescence generation. Without wishing to be bound by theory, the pH response of pHAM may originate from both homoFRET and PET mechanisms as a result of the cooperative neutralization and micellization of the block copolymers (see e.g. FIG. 1C). Compared with small molecular pH-sensitive dyes or PET-based micelles (activations need 2 pH units), the sharpened pH response from pHAM may result in complete turn-ON of the fluorophores with subtle changes of pH in tumor microenvironment (pH$_e$=6.5-6.9) or intracellular organelles (5.0-6.2).

The micelles may have different pH transition values within physiological range, in order to target specific cells or microenvironments. In some embodiments, the micelles have a pH transition value of about 5 to about 8. In some embodiments, the micelles have a pH transition value of about 5 to about 6. In some embodiments, the micelles have a pH transition value of about 6 to about 7. In some embodiments, the micelles have a pH transition value of about 7 to about 8. In some embodiments, the micelles have a pH transition value of about 6.3 to about 6.9 (e.g. tumor microenvironment). In some embodiments, the micelles have a pH transition value of about 5.0 to about 6.2 (e.g. intracellular organelles). In some embodiments, the micelles have a pH transition value of about 5.9 to about 6.2 (e.g. early endosomes). In some embodiments, the micelles have a pH transition value of about 5.0 to about 5.5 (e.g. late endosomes or lysosomes). As described in the Examples, nanoprobes 4, 3, 7 and 6 had fluorescence transition pH values of 5.4, 6.3, 6.8 and 7.2, respectively.

Labeled micelles of the invention may advantageously have a large signal response (e.g. a larger difference in signal between ON and OFF states). For example, when fluorescent labels are used, the ratio of $F_{max}$ and $F_{min}$ ($R_F = F_{max}/F_{min}$) can be used to quantify the fluorescence response between the ON/OFF states. As shown in the Examples, nanoprobes having $R_F$ values in the range of 10 to 55 fold were made (Table 3), demonstrating the large fluorescence response of the nanoprobes. In various embodiments, labeled micelles have a signal response of at least about 10, at least about 20, at least about 30, at least about 40, at least about 50, at least about 60.

Without wishing to be bound by theory, the use of micelles in cancer therapy may enhance anti-tumor efficacy and reduce toxicity to healthy tissues, in part due to the size of the micelles. While small molecules such as certain chemotherapeutic agents (e.g. doxorubicin) can enter both normal and tumor tissues, non-targeted micelle nanoparticles may preferentially cross leaky tumor vasculature (see e.g. FIG. 15). In some embodiments, the micelles have a size of about 10 to about 200 nm. In some embodiments, the micelles have a size of about 20 to about 100 nm. In some embodiments, the micelles have a size of about 30 to about 50 nm.

Examples of methods of generating micelles from block copolymers may be found in the Examples below. For example, block copolymer is first dissolved in organic solvent (e.g. THF) and may be added to an aqueous solution, optionally under sonication, wherein the copolymer self-assemble to form micelles in the solution.

In some embodiments, the micelle further comprises a drug. In some embodiments, the micelle further comprises a labeling moiety. In some embodiments, the micelle further comprises a targeting moiety. In some embodiments, the micelle further comprises a drug and a labeling moiety. In some embodiments, the micelle further comprises a drug and a targeting moiety. In some embodiments, the micelle further comprises a targeting moiety and a labeling moiety. In some embodiments, the micelle further comprises a drug, a targeting moiety, and a labeling moiety.

Targeting Moieties

The micelles may further optionally comprise a targeting moiety in therapeutic or diagnostic applications. For example, a targeting moiety can target a cancer cell surface marker, such as an angiogenesis biomarker. For example, in diagnostic applications, targeted nanoprobes may be useful for diagnosing tumors and/or the efficacy assessment of molecular-targeted antiangiogenic therapies, where the expression levels of the therapeutic targets (e.g. VEGFR2, $\alpha_v\beta_3$) can be specifically measured.

In some embodiments, the targeting moiety binds to an angiogenesis biomarker. In some embodiments, the angiogenesis biomarker is VEGF-VEGFR complex or endoglin. In some embodiments, the targeting moiety binds to VEGFR2. In some embodiments, the targeting moiety is a Fab' fragment of RAFL-1 mAb. In some embodiments, the targeting moiety binds to 43 integrin. In some embodiments, the targeting moiety is cRGDfK.

The targeting moiety may be conjugated to the block copolymer (e.g., the hydrophilic polymer segment) by methods known in the art. Examples of conjugation may be found in the Examples below.

Drug Encapsulation

The micelles may further optionally comprise a drug encapsulated within the micelle. Due to the hydrophobic interior of the micelle, hydrophobic drugs may be more readily encapsulated within the micelles. In some embodiments, the drug is hydrophobic and has low water solubility. In some embodiments, the drug has a log p of about 2 to about 8. In some embodiments, the drug is a chemotherapeutic agent. In some embodiments, the drug is doxorubicin. In some embodiments, the drug is β-lapachone. In some embodiments, the drug is paclitaxel.

The drug may be incorporated into the micelles using methods known in the art, such as solvent evaporation. Examples of drug incorporation may be found in, e.g. Example 4 below. Briefly, for example, drug may be encapsulated in micelles by first dissolving the drug and the block co-polymer in organic solution. Addition of this solution to an aqueous solution, optionally under sonication, may result in micelle-encapsulated drug.

Therapeutic and Diagnostic Methods

Micelles comprising a drug may be used to treat e.g. cancers, cardiovascular disease, inflammation, an autophagy-related disease, or lysosomal storage disease, or other diseases wherein the drug may be delivered to the appropriate location due to localized pH differences (e.g. a pH different from physiological pH (7.4)). Micelles for therapeutic methods may optionally further comprise a labeling moiety (e.g. to assist in the imaging of the treatment) and/or a targeting moiety (e.g. to target a specific cell surface marker or to target the micelles for endocytic delivery). In some embodiments, the disorder treated is a cancer. In some embodiments, the cancer comprises a solid tumor. In embodiments wherein the micelle comprises a targeting moiety, non-solid cancers may be treated. In some embodiments, the disorder treated is lysosomal storage disease. In some embodiments, the micelles have a pH transition value of about 6.3 to about 7.2 (e.g. for delivery to the tumor microenvironment). In some embodiments, the micelles have a pH transition value of about 5.0 to about 6.5 (e.g. for delivery to intracellular organelles). In some embodiments, the micelles have a pH transition value of about 6.2 or above 6.2 (e.g. for delivery to early endosomes). In some embodiments, the micelles have a pH transition value of about 5.5 (e.g. for delivery to late endosomes or lysosomes). In some embodiments, the micelles have a pH transition value of about 6.3 to about 6.9. In some embodiments, the micelles have a pH transition value of about 5.0 to about 6.2. In some embodiments, the micelles have a pH transition value of about 5.9 to about 6.2. In some embodiments, the micelles have a pH transition value of about 5.0 to about 5.5. As described in the Examples, nanoprobes 4, 3, 7 and 6 have fluorescence transition pH values of 5.4, 6.3, 6.8 and 7.2, respectively. In some embodiments, non-targeted pHAM with higher $pH_t$ (e.g. 7.2, 6.8) may be used to delivery drug to tumors. In some embodiments, targeted pHAM with lower $pH_t$ (e.g. 5.4, 6.3) may be used to delivery drug to endocytic compartments.

Micelles comprising a labeling moiety may be used in imaging applications, for example, imaging tumors or endocytic compartments. Micelles for diagnostic methods may optionally further comprise a targeting moiety (e.g. to target a specific cell surface marker or to target the micelles for endocytic delivery). In some embodiments, the method is used to diagnose a tumor in the individual. In some embodiments, the method is used to monitor a tumor in the individual, for example to monitor the effects of a treatment. In some embodiments, the micelle is used for imaging early endosomal activity. In some embodiments, the micelle is used for imaging late endosomal activity. In some embodiments, the micelle is used for imaging lysosomal activity. In some embodiments, the micelles have a pH transition value of about 6.3 to about 7.2 (e.g. for delivery to the tumor microenvironment). In some embodiments, the micelles have a pH transition value of about 5.0 to about 6.5 (e.g. for delivery to intracellular organelles). In some embodiments, the micelles have a pH transition value of about 6.2 or above 6.2 (e.g. for delivery to early endosomes). In some embodiments, the micelles have a pH transition value of about 5.5

(e.g. for delivery to late endosomes or lysosomes). In some embodiments, the micelles have a pH transition value of about 6.3 to about 6.9 (e.g. for imaging the tumor microenvironment). In some embodiments, the micelles have a pH transition value of about 5.0 to about 6.2 (e.g. for imaging intracellular organelles). In some embodiments, the micelles have a pH transition value of about 5.9 to about 6.2 (e.g. for imaging early endosomes). In some embodiments, the micelles have a pH transition value of about 5.0 to about 5.5 (e.g. for imaging late endosomes or lysosomes). As described in the Examples, nanoprobes 4, 3, 7 and 6 have fluorescence transition pH values of 5.4, 6.3, 6.8 and 7.2, respectively. In some embodiments, non-targeted pHAM with higher $pH_t$ (e.g. 7.2, 6.8) may be used for imaging tumors. In some embodiments, targeted pHAM with lower $pH_t$ (e.g. 5.4, 6.3) may be used for imaging endocytic compartments, or for imaging tumors via endocytic uptake.

More than one type of label may be used in the compositions of the invention. For example, different NIR fluorophores (e.g. with distinctive excitation/emission wavelengths) may be used to generate a series of multi-chromatic nanoprobes for different biomarkers. This creates a multi-chromatic set of nanoprobes that allow the simultaneous imaging of several molecular targets (e.g. VEGFR2 and $\alpha_\nu\beta_3$) which may further improve the imaging efficacy of angiogenic tumor vasculature.

The invention further provides a composition comprising a micelle and a pharmaceutically acceptable carrier. Such composition may be administered to the individual by any suitable method, such as, for example, injection (e.g. intravenous injection) or infusion. Administration may be local or systemic.

The following examples are provided for illustrative purposes only and are not intended to limit the scope of the invention in any manner. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention.

EXAMPLES

Unless indicated otherwise, temperature is in degrees Centigrade and pressure is at or near atmospheric pressure.

Example 1

Synthesis of Tunable, pH-Activatable Micellar (pHAM) Nanoparticles

I. Syntheses of Methacrylate Monomers 2-(Tetramethyleneimino) ethanol (C5A), 2-(pentamethyleneimino) ethanol (C6A) and N,N,N',N'',N''-pentamethyldiethylenetriamine (PMDETA) were purchased from Sigma-Aldrich. 2-(Hexamethyleneimino) ethanol (C7A) and 2-(dibutylamino) ethanol (DBA) were purchased from Alfa Aesar Company and TCI America Inc., respectively. NHS-tetramethyl rhodamine (NHS-TMR) was purchased from Invitrogen Company. Monomers 2-(dimethylamino)ethyl methacrylate (DMA-MA), 2-(diethylamino)ethyl methacrylate (DEA-MA), 2-(diisopropyl amino)ethyl methacrylate (DPA-MA) and 2-aminoethyl methacrylate (AMA) were purchased from Polyscience Company. AMA was recrystallized twice with isopropanol and ethyl acetate (3:7). PEG macroinitiator, MeO-PEG114-Br, was prepared from 2-bromo-2-methyl propanoyl bromide and MeO-PEG114-OH according to the procedure in literature (Bronstein et al., *J. Phys. Chem. B,* 2005, 109:18786-18798). Other solvents and reagents were used as received from Sigma-Aldrich or Fisher Scientific Inc.

All new methacrylate monomers (C5A-MA, C6A-MA, C7A-MA, DBA-MA) were synthesized following a similar method. Synthesis of 2-(pentamethyleneimino)ethyl methacrylate (C6A-MA) is described as a representative procedure. First, 2-(pentamethyleneimino)ethanol (12.9 g, 0.1 mol), triethylamine (10.1 g, 0.1 mol), and inhibitor hydroquinone (0.11 g, 0.001 mol) were dissolved in 100 mL Tetrahydrofuran (THF) and then methacryloyl chloride (10.4 g, 0.1 mol) was added dropwise into a three-neck flask. The solution was refluxed in THF for 2 hrs. After reaction, the solution was filtered to remove the precipitated triethylamine-HCl salts, and THF solvent was removed by rotovap. The resulting residue was distilled in vacuo (83~87° C. at 0.05 mm Hg) as a colorless liquid. After syntheses, the monomers were characterized by $^1$H NMR. All the NMR spectra were obtained in CDCl$_3$ using tetramethylsilane (TMS) as the internal reference on a Varian 500 MHz $^1$H NMR spectrometer. The characterization and yield for the monomers are as following are shown in Table 1.

TABLE 1

Characterization and yield for methacrylate monomers.

| Methacrylate Monomer | Characterization |
|---|---|
| ![C5A-MA structure]<br>C5A-MA<br><br>2-(Tetramethyleneimino)ethyl methacrylate<br>(C5A-MA) | $^1$H NMR (TMS, CDCl$_3$, ppm): 6.09 (br, 1H, CHH═C(CH$_3$)—), 5.54 (br, 1H, CHH═C(CH$_3$)—), 4.26 (t, J = 6.2 Hz, 2H, —OCH$_2$CH$_2$N—), 2.76 (t, J = 6.2 Hz, 2H, —OCH$_2$CH$_2$N—), 2.56 (m, 2H, —N(CH$_2$CH$_2$)$_2$), 1.92 (s, 3H, CH$_2$═C(CH$_3$)—), 1.73 (m, 4H, —N(CH$_2$CH$_2$)$_2$).<br>Yield: 78% |

TABLE 1-continued

Characterization and yield for methacrylate monomers.

| Methacrylate Monomer | Characterization |
|---|---|
| 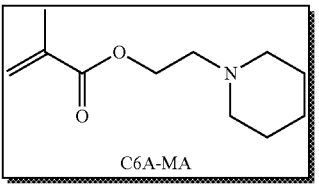<br>2-(Pentamethyleneimino) ethyl methacrylate<br>(C6A-MA) | $^1$H NMR (TMS, CDCl$_3$, ppm): 6.04 (br, 1H, CHH═C(CH$_3$)—), 5.50 (br, 1H, CHH═C(CH$_3$)—), 4.22 (t, J = 6.4 Hz, 2H, —OCH$_2$CH$_2$N—), 2.60 (t, J = 6.5 Hz, 2H, —OCH$_2$CH$_2$N—), 2.40 (m, 4H, —N(CH$_2$CH$_2$)$_2$CH$_2$), 1.88 (s, 3H, CH$_2$═C(CH$_3$)—), 1.52 (m, 4H, —N(CH$_2$CH$_2$)$_2$CH$_2$), 1.36 (m, 2H, —N(CH$_2$CH$_2$)$_2$CH$_2$).<br>Yield: 70% |
| 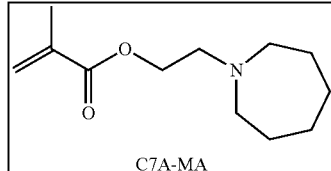<br>2-(Hexamethyleneimino)ethyl methacrylate<br>(C7A-MA) | $^1$H NMR (TMS, CDCl$_3$, ppm): 6.09 (br, 1H, CHH═C(CH$_3$)—), 5.55 (br, 1H, CHH═C(CH$_3$)—), 4.24 (t, J = 6.5 Hz, 2H, —OCH$_2$CH$_2$N—), 2.84 (t, J = 6.5 Hz, 2H, —OCH$_2$CH$_2$N—), 2.72 (m, 4H, —N(CH$_2$CH$_2$CH$_2$)$_2$), 1.94 (s, 3H, CH$_2$═C(CH$_3$)—), 1.63 (m, 4H, —N(CH$_2$CH$_2$CH$_2$)$_2$), 1.58 (m, 4H, —N(CH$_2$CH$_2$CH$_2$)$_2$).<br>Yield: 54% |
| 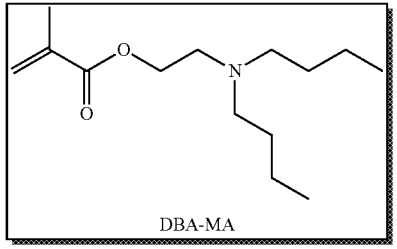<br>2-(Dibutylamino)ethyl methacrylate<br>(DBA-MA) | $^1$H NMR (TMS, CDCl$_3$, ppm): 6.09 (br, 1H, CHH═C(CH$_3$)—), 5.55 (br, 1H, CHH═C(CH$_3$)—), 4.19 (t, J = 6.3 Hz, 2H, —OCH$_2$CH$_2$N—), 2.73 (t, J = 6.3 Hz, 2H, —OCH$_2$CH$_2$N—), 2.46 (t, J = 7.6 Hz, 2H, —N(CH$_2$CH$_2$CH$_2$CH$_3$)$_2$), 1.93 (s, 3H, CH$_2$═C(CH$_3$)—), 1.41 (m, 4H, —N(CH$_2$CH$_2$CH$_2$CH$_3$)$_2$), 1.29 (m, 4H, —N(CH$_2$CH$_2$CH$_2$CH$_3$)$_2$), 0.89 (t, J = 7.3 Hz, 6H, —N(CH$_2$CH$_2$CH$_2$CH$_3$)$_2$).<br>Yield: 53% |

II. Synthesis of PEO-b-PR and PEO-b-(PR-r-TMR) Block Copolymers

Figure 1A:
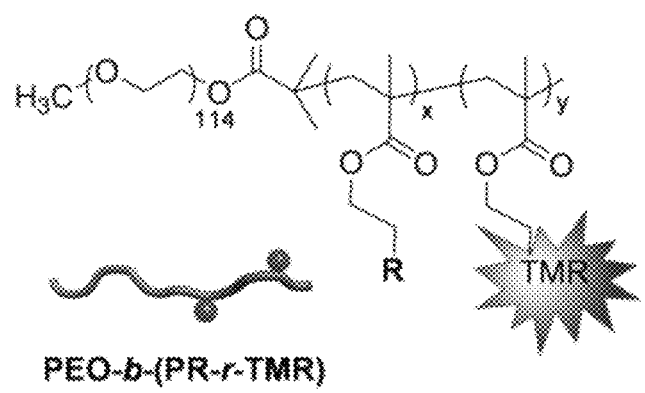
FIGS. 1A and 1B illustrate examples of block copolymers of the invention.
Figure 1B:
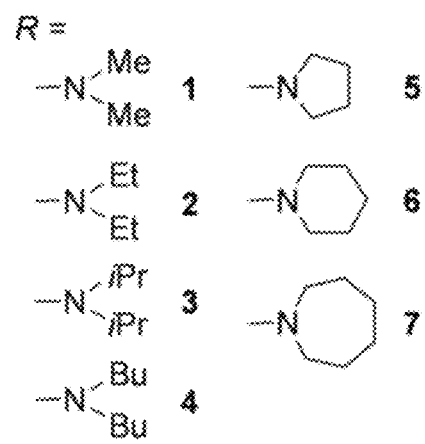
Figure 1C:
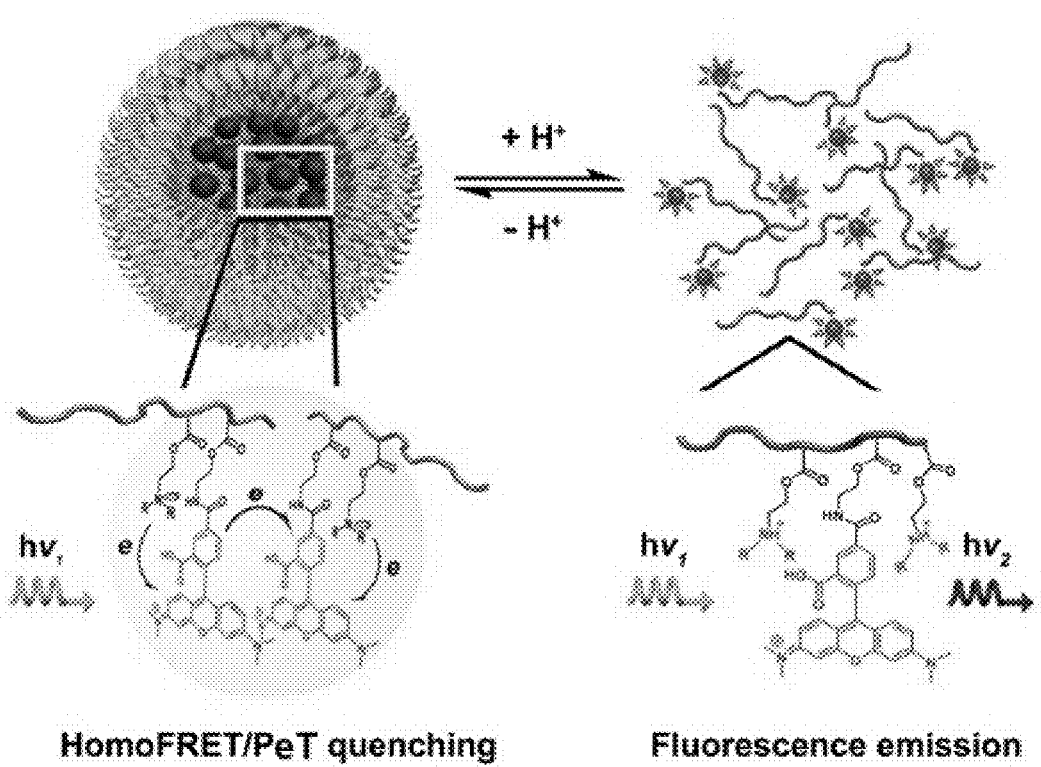
FIG. 1C illustrates the design principle of an example of a micelle comprising a fluorescent label (using TMR as an example). At high pH, micelle assembly results in fluorescence quenching due to homoFRET and photoinduced electron transfer (PET) mechanisms. At low pH, micelle disassembly leads to dramatic increase in emission. At high pH, the amine in the hydrophobic polymer segment is not protonated. At low pH, the amine group in the hydrophobic polymer segment is protonated.

Two series of block copolymers (PEO-b-PR (y=0) and PEO-b-PR-r-TMR, FIG. 1A) with different tertiary amine-containing segments (PR) and poly(ethylene oxide) (PEO) segments were made by atom transfer radical polymerization (ATRP; Tsarevsky & Matyjaszewski, Chem. Rev. 2007, 107:2270-2299; Ma et al., Macromolecules 2003, 36:3475-3484). In the linear di-alkyl series (see FIG. 1B, R groups 1, 2, 3, and 4) the chain length was varied from methyl to butyl groups; in the cyclic series (see FIG. 1B, R groups 5, 6 and 7), the ring size from 5- to 7-membered rings was varied.

A pH-insensitive dye, tetramethyl rhodamine (TMR; Albertazzi et al. Am. Chem. Soc. 2010, 132:18158-18167) was used as a model fluorophore and conjugated in the PR block as an imaging beacon to investigate the pH responsive properties of pHAM nanoparticles. As described in more detail below, at higher pH, neutral PR segments co-operatively self-assemble into the hydrophobic cores of micelles, which results in the aggregation of fluorophores and quenching of fluorescent signals through mechanisms of Förster resonance energy transfer between TMR molecules (homo-FRET) and photoinduced electron transfer (PeT) from tertiary amines to TMR (Kobayashi et al., Chem. Rev. 2010, 110:2620-2640; Uchiyama et al., Chem. Int. Ed. 2008, 47:4667-4669; Lakowicz, Principles of Fluorescence Spectroscopy, 3rd ed., Springer, New York City, 2006, pp. 443-475; Diaz-Fernandez et al., Chem. Eur. J. 2006, 12:921-930). At lower pH, PR segments become protonated and positively charged, leading to micelle disassembly and dramatic increase in fluorescence emission due to the increase in TMR distance and decrease in PeT (FIG. 1C)).

PEO-b-PR copolymers (FIG. 2A) were first synthesized by atom transfer radical polymerization (ATRP) method. The dye-free copolymers were used in polymer characterizations and measurement of pKa and critical micelle concentrations (Tables 2 and 3). PEO-b-PDPA is used as an example to illustrate the procedure. First, DPA-MA (1.06 g, 5 mmol), PMDETA (21 µL, 0.1 mmol), and MeO-PEG$_{114}$-Br (0.5 g, 0.1 mmol) were charged into a polymerization tube. Then a mixture of 2-propanol (2 mL) and DMF (2 mL) was added to dissolve the monomer and initiator. After three cycles of freeze-pump-thaw to remove oxygen, CuBr (14 mg, 0.1 mmol) was added into the reaction tube under nitrogen atmosphere, and the tube was sealed in vacuo. The polymerization was carried out at 40° C. for 8 hrs. After polymerization, the reaction mixture was diluted with 10 mL THF, and passed through an Al$_2$O$_3$ column to remove the catalyst. The THF solvent was removed by rotovap. The residue was dialyzed in distilled water and lyophilized to obtain a white powder. The resulting PEO-b-PR copolymers were characterized by $^1$H 500 MHz NMR, gel permeation chromatography (Viscotech GPCmax, PLgel 5 µm MIXED-D columns by Polymer Labs, THF as eluent at 1 mL/min). Table 2 lists the yield, molecular weights ($M_n$ and $M_w$) and polydispersity index (PDI) of each copolymer. PEO-b-PDPA (without labeling moiety) indicates block copolymer (3), PEO-b-PDBA (without labeling moiety) indicates block copolymer (4), PEO-b-PC6A (without labeling moiety) indicates block copolymer (6), and PEO-b-PC7A (without labeling moiety) indicates block copolymer (7).

TABLE 2

Characterization of PEO-b-PR diblock copolymers.

| Co-polymer | Yield (%) | $M_{w, GPC}$ (×10$^{-4}$ D)$^a$ | $M_{n, GPC}$ (×10$^{-4}$ D)$^a$ | PDI$^a$ | Repeating units in the PR block$^b$ | $M_{n,{}^1H\ NMR}$ (×10$^{-4}$)$^b$ |
|---|---|---|---|---|---|---|
| 1 | 71 | 1.47 | 1.36 | 1.08 | 61 | 1.46 |
| 2 | 62 | 1.91 | 1.75 | 1.09 | 58 | 1.57 |
| 3 | 71 | 1.14 | 1.04 | 1.10 | 45 | 1.46 |
| 4 | 81 | 1.24 | 1.04 | 1.19 | 51 | 1.73 |
| 5 | 73 | 1.41 | 1.26 | 1.12 | 49 | 1.40 |
| 6 | 65 | 1.61 | 1.38 | 1.17 | 45 | 1.38 |
| 7 | 78 | 1.83 | 1.40 | 1.31 | 49 | 1.54 |

$^a$Number-averaged ($M_n$), weight-averaged molecular weight ($M_w$) and polydispersity index (PDI = $M_w/M_n$) were determined by GPC using THF as the eluent;
$^b$Determined by $^1$H NMR.

Figure 2A:
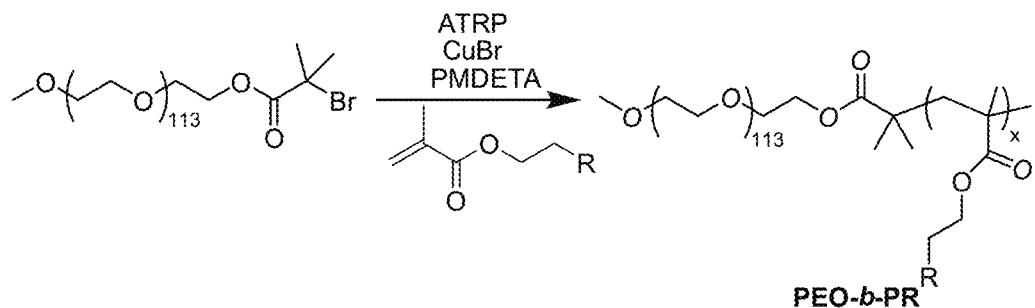
FIG. 2A illustrates an example of synthesis PEO-b-PR copolymers by atom transfer radical polymerization (ATRP) method.
Figure 2B:
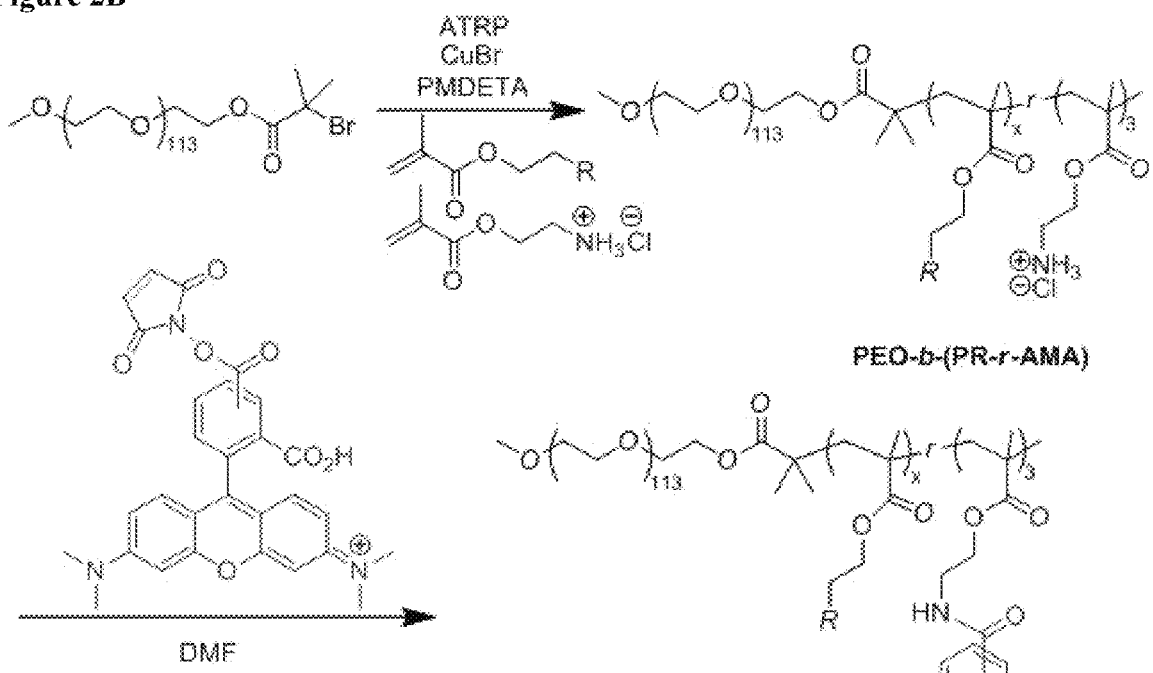
FIG. 2B illustrates an example of synthesis of PEO-b-(PR-r-TMR) nanoprobes.

To introduce the TMR dye, AMA was used in the copolymer synthesis (FIG. 2B). Synthesis of PEO-b-(PR-r-AMA) copolymers followed the procedure described above. Three primary amino groups were introduced into each polymer chain by controlling the feeding ratio of the AMA monomer to the initiator (ratio=3). Similar yields and molecular weights were obtained for these PEO-b-(PR-r-AMA) copolymers. For TMR conjugation, PEO-b-(PR-r-AMA) (50 mg) was first dissolved in 2 mL DMF. Then NHS-TMR ester (1.5 equivalents to the molar amount of the primary amino group) was added. The reaction mixture was stirred at room temperature for two days. The copolymers were purified by preparative gel permeation chromatography (PLgel Prep 10 μm 10E3A 300×25 mm columns by Varian, THF as eluent at 5 mL/min) to remove the free dye molecules. The produced PEO-b-(PR-r-TMR) copolymers were lyophilized and kept at −20° C. for storage. In the TMR-containing copolymers, the number of repeating units in the PR block was 70.

III. Preparation of Micelle Nanoparticles

Micelles were prepared following a solvent evaporation method as previously published (Nasongkla et al., *Nano. Lett.* 2006, 6:2427-2430). In the example of PEO-b-(PDPA-r-TMR), 24 mg of the copolymer was first dissolved in 1 mL THF and then added into 4 mL distilled water dropwise under sonication. The THF was allowed to evaporate for 4 hrs by air stream. Then distilled water was added to adjust the polymer concentration to 4 mg/mL as a stock solution. After micelle formation, the nanoparticles were characterized by transmission electron microscopy (TEM, JEOL 1200 EX model) for micelle size and morphology, dynamic light scattering (DLS, Malvern MicroV model, He—Ne laser, λ=632 nm) for hydrodynamic diameter ($D_h$).

Example 2

Characterization of Tunable, pH-Activatable Micellar Nanoparticles

Synthesized micellar nanoparticles were characterized to demonstrate their pH-responsive properties both for pH response in the physiological range (5.0-7.4) as well as for their temporal response.

I. Fluorescence Characterizations

In this study, conjugated TMR fluorophore was used as an imaging beacon to investigate the pH-responsive properties of pHAM nanoparticles. (Polyethylene oxide)-b-poly((dimethyl-amino)ethyl methacrylate) (PEO-b-PDMA, (1) was used as an "always ON" control where no micelles or fluorescence quenching was observed in the tested pH range (4.5-8.0) due to the strong hydrophilicity of the PDMA block. First, fluorescence emission spectra of pHAM nanoprobes (3, 4, 6, 7) and PEO-b-(PDMA-r-TMR) were obtained on a Hitachi fluorometer (F-7500 model). For each copolymer, the sample was initially prepared in MilliQ water at the concentration of 6 mg/mL. Then the stock solution was diluted in 0.2 M citric-phosphate buffers with different pH values. The terminal polymer concentration was controlled at 0.1 mg/mL. The nanoprobe was excited at 545 nm, and the emission spectra were collected from 560 to 700 nm. The emission and excitation slits were both 5 nm.

For fluorescence lifetime measurements, the fluorescence decays of TMR from PEO-b-(PDPA-r-TMR) (3) and PEO-b-(PDBA-r-TMR) (4) (both at 0.1 mg/mL) were measured. For nanoprobe 3 (pH$_t$=6.3), the life times were measured at pH=7.4 and 5.5 (above and below the pH$_t$, respectively) in sodium phosphate/citric acid buffers. Similarly, for nanoprobe 4 (pH$_t$=5.4), the life times were measured at pH=7.4 and 4.9. In both experiments, free TMR dye (0.005 mg/mL) was also measured as a control. These studies were carried out on a LaserStrobe fluorescence lifetime instrument (Photon Technology International, Inc., Birmingham, N.J.), which consists of a nitrogen laser (GL-3300) linked to a dye laser (GL 302) and a stroboscopic detector. C-540A (Exciton, Inc., Dayton, Ohio) dye solution was used to generate an excitation wavelength of 540 nm. The decay curves were analyzed at the wavelength of 570 nm. The emission monochromator slit was at 4 nm. All measurements were conducted at room temperature. The IRF (instrument response function) was determined by measuring scattered light from a solution of glycogen. The fluorescence intensity decay data were analyzed by the single exponential decay function, using the software supplied with the PTI instrument.

Fluorescent images of a series of nanoprobe solutions at different pH values illustrate a sharp fluorescence transition for each nanoprobe, illustrating the tunable, ultra pH responsive properties of pHAM nanoprobes.

Figure 3A:
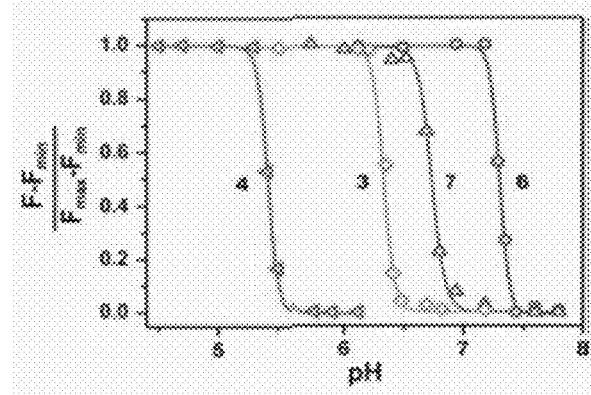
FIG. 3A shows the normalized fluorescence intensity of pHAM nanoprobes 3, 4, 6, 7 as a function of pH. The pH response ($\Delta pH_{10-90\%}$) was <0.25 pH unit and $F_{max}/F_{min}$ was up to 55 fold.

Normalized fluorescence intensity (NFI) vs. pH curves (FIG. 3A) permitted quantitative assessment of the pH responsive properties of the pHAM nanoprobes. NFI was calculated as the ratio of $[F-F_{min}]/[F_{max}-F_{min}]$, where F was the fluorescence intensity of the nanoprobe at any given pH, and $F_{max}$ and $F_{min}$ was the maximal and minimal fluorescence intensities at the ON/OFF states, respectively. The emission intensity at 580 nm was used to quantify the ultra-pH response for different pHAM nanoprobes as shown in FIG. 3A. To quantify the sharpness in pH response, $\Delta pH_{10\text{-}90\%}$, the pH range in which the NFI value varies from 10% to 90%, for all the pHAM nanoprobes was evaluated. The sharpness values were 0.21, 0.23, 0.24, and 0.20 pH unit for nanoprobes 4, 6, 3 and 7, respectively.

The small values of $\Delta pH_{10\text{-}90\%}$ indicate a remarkable pH sensitivity as it represents a <2-fold change in proton concentration (i.e. $[H^+]_{10\%}/[H^+]_{90\%}=10^{\Delta pH10\text{-}90\%}$). In comparison, for small molecular dyes (Urano, et al., *Nat. Med.* 2009, 15:104-109), the sharpness value is about 2 pH unit (100-fold in $[H^+]$) for the same degree of emission change, consistent with Henderson-Hasselbalch equation (Atkins & De Paula, *Physical Chemistry*, Oxford University Press, 2009). In addition to the pH sharpness, the ratio of $F_{max}$ and $F_{min}$ ($R_F=F_{max}/F_{min}$) was also measured to quantify the fluorescence response between the ON/OFF states. The values of $R_F$ range from 10 to 55 fold (Table 3), demonstrating the large fluorescence response of the nanoprobes. Consistent with the decreased emission intensity in the micelles, the data demonstrated that excited state of TMR had a much shorter life time (e.g. 0.44 ns for nanoprobe 3, in the micelles (pH=7.4) than the free dye (1.97 ns) at pH 7.4 or the disassembled unimers at pH 5.5 (1.84 ns).

TABLE 3

Characterization of PEO-b-(PR-r-TMR) nanoprobes.

| Co-polymer | pKa[a] Monomer | pKa[a] Polymer | CMC[b] (mg/mL) | $D_h$ (nm)[c] | $R_F$ ($F_{max}/F_{min}$)[d] | $\Delta pH_{10-90\%}$ | $\tau_{1/2}$ (ms)[e] |
|---|---|---|---|---|---|---|---|
| 1 | 8.4 | 7.4 | — | — | 1.0 | — | — |
| 2 | 9.2 | 7.4 | — | — | 1.8 | — | — |
| 3 | 8.5 | 6.3 | 0.001 | 41 | 55 | 0.20 | 3.2 ± 0.1 |
| 4 | 6.9 | 5.1 | 0.003 | 43 | 20 | 0.17 | 3.9 ± 0.1[f] |
| 5 | 9.1 | 7.6 | — | — | — | — | — |
| 6 | 8.9 | 6.9 | 0.004 | 39 | 10 | 0.17 | 2.7 ± 0.1 |
| 7 | 8.6 | 6.7 | 0.003 | 38 | 23 | 0.23 | 3.0 ± 0.2 |

[a]Determined by pH titration experiments.
[b]Determined by $I_1/I_3$ ratio of pyrene probe at pH 7.4;
[c]Determined by DLS at copolymer concentration of 1 mg/mL and pH = 7.4;
[d]Determined by rhodamine fluorescence emission intensity;
[e]Determined by stopped-flow measurement by mixing 20 μL 5 mg/mL polymer solution with 80 μL phosphate buffer at pH 5.5;
[f]pH = 4.9 buffer was used to account for the low pH$_t$ value of 4 (5.4).

In summary, pH-activatable micellar nanoparticles demonstrate tunability and ultra-sensitive pH response in the physiological range (pH 5.0-7.4), large increases in emission intensity between ON/OFF states (up to 55 times), and only require <0.25 pH for activation.

II. pH Temporal Response

This study used stopped-flow measurements to gauge fluorescence activation in synthesized pH-activatable micellar nanoparticles. Stopped-flow measurements of pHAM nanoprobes were conducted using a Bio-Logic SFM-3 instrument. All experiments were carried out at room temperature at different pH values in the sodium phosphate/citric acid buffer. A monochromator was used for excitation at 540 nm and the fluorescence intensity at 570 nm long pass was recorded. Experiments were controlled by BioKine 16 V 3.03 software and had an estimated dead time of 1.5 ms.

Figure 3B:
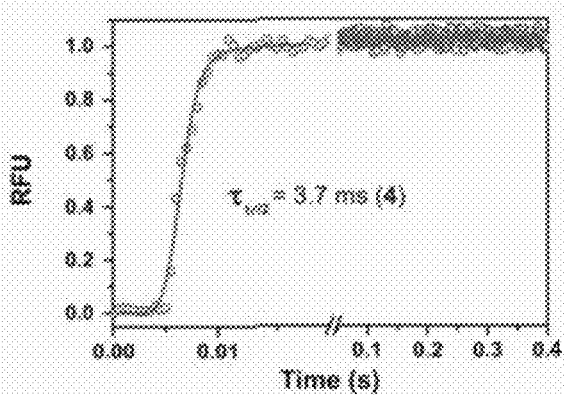
FIG. 3B shows stopped-flow fluorescence measurement of nanoprobe 4 ($pH_t$=5.4) after pH activation at 4.9. Fluroesence recovery time ($\tau_{1/2}$) was 3.7 ms.

The stopped-flow experiments showed that fluorescence activation was very fast, with most nanoprobes fully activated within 5 ms at lower pH (e.g. $\tau_{1/2}$=3.7 ms for 4, FIG. 3B). The ultra-sensitive pH response was only observed with nanoprobes 4, 3, 7 and 6. The fluorescence transition pH values (pH$_t$, the pH at which $F=0.5\times(F_{max}+F_{min})$) were 5.4, 6.3, 6.8 and 7.2 for nanoprobes 4, 3, 7 and 6, respectively (FIG. 3A). The other copolymers either did not show any pH response (e.g., 1) or only broad pH responses (e.g. 2, 5, data not shown).

In summary, the stopped-flow experiments demonstrated that the pH-activatable micellar nanoparticles have fast temporal response in the range of less than 5 ms.

Figure 4A:
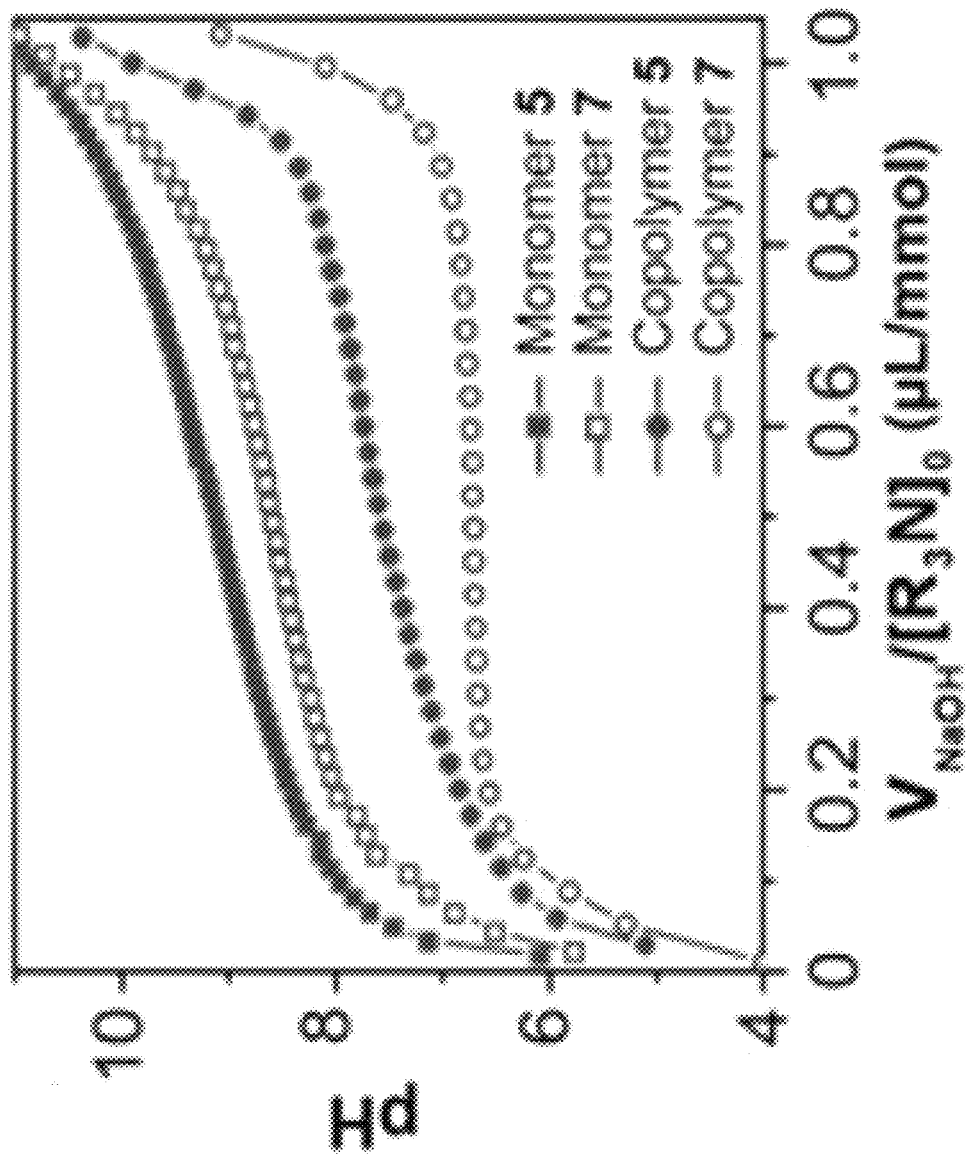
FIG. 4A shows the pH titration curves of two representative PEO-b-PR block copolymers, 5 and 7, and their corresponding monomers.

III. pH Titration Curves of Copolymers and Constituent Monomers and Subsequent $^1$H NMR Spectra Analysis Without being bound to theory, it is believed that hydrophobic micellization is the driving force of the ultra-pH responsive properties of pHAM, and a critical threshold of hydrophobicity in the PR segment is necessary to achieve the co-operative response. To test this hypothesis, the pH titration curves of two representative block copolymers, 5 and 7, and their corresponding monomers were compared (FIG. 4A).

In a typical procedure, a PEO-b-PR copolymer or its corresponding monomer was first dissolved in 0.1 N HCl to reach the final concentration of 5-10 mg/mL. pH titration was carried out by adding small volumes (50-100 μL increments) of 0.1 N NaOH solution under stirring. The pH increase in the range of 2 to 11 was monitored as a function of total added volume of NaOH ($V_{NaOH}$). The pH values were measured using a Mettler Toledo pH meter with a microelectrode. FIG. 4A shows the representative titration curves for the cyclic PEO-b-PR copolymers (5 and 7) and corresponding monomers. For each sample, the pKa value was calculated as the pH in the middle of the two equivalence points in the titration curve. The pKa values for all the PEO-b-PR copolymers and corresponding monomers were listed in Table 3.

Figure 4B:
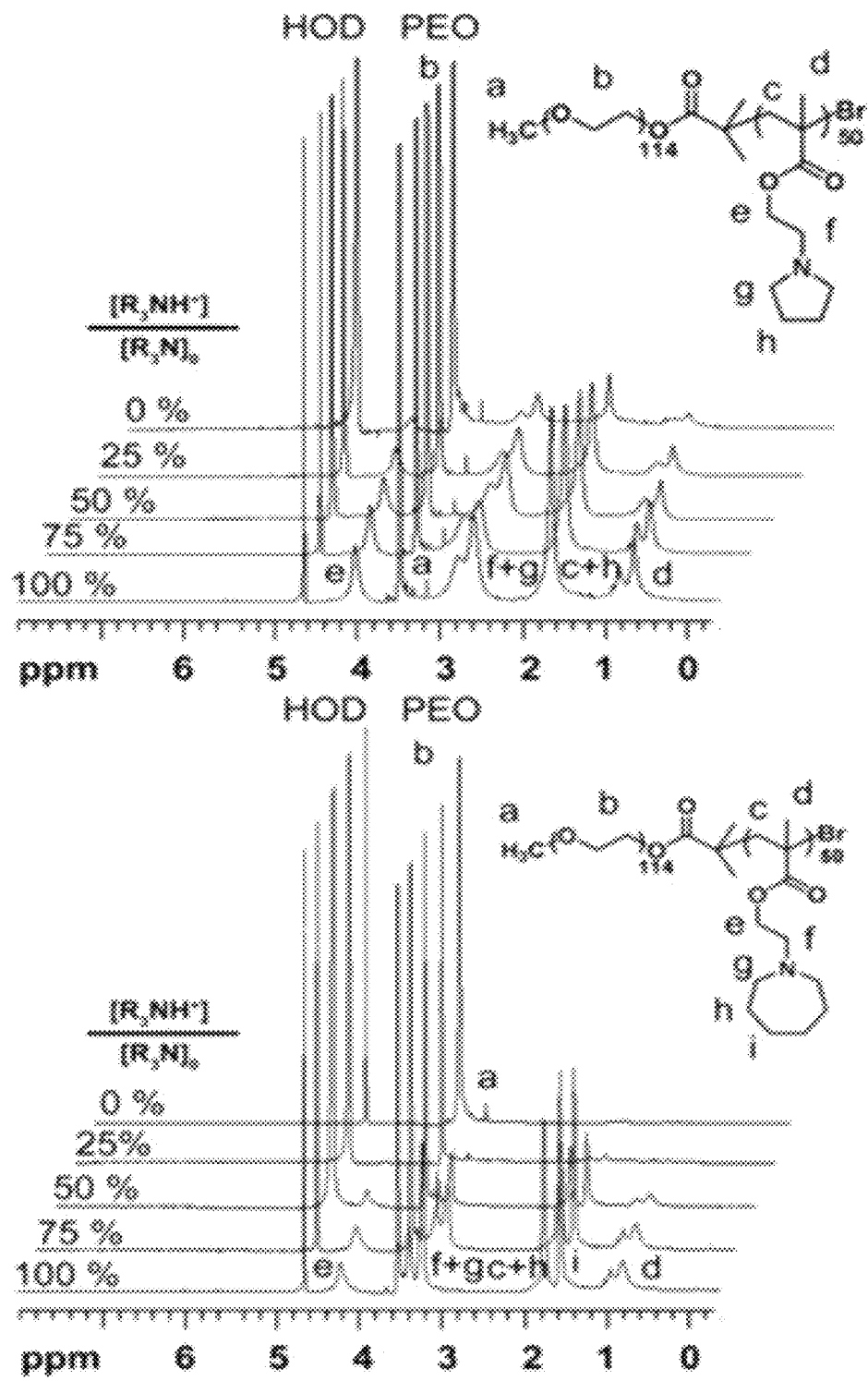
FIG. 4B shows deuterated $^1H$ NMR spectra of two representative PEO-b-PR block copolymers, 5 and 7, at different ionization states of tertiary amines.
Figure 4C:
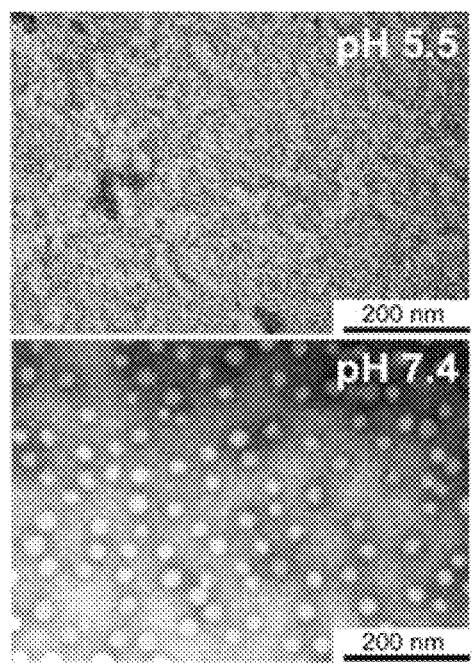
FIG. 4C shows transmission electron microscopy (TEM) of PEO-b-PR block copolymer 7 in aqueous solution, demonstrating the formation of micelles above its pKa (6.7) at pH 7.4 and complete micelle dissociation at pH 5.5. Average diameter of micelles was 45 nm.

Both monomers behaved like small ionizable molecules with broad pH responses over added volumes of NaOH. Copolymer 5 showed a similar broad pH response. In contrast, copolymer 7 had a dramatically sharpened pH transition, demonstrating a greatly increased buffer capacity. Deuterated $^1$H NMR spectra of 5 and 7 at different ionization states of tertiary amines ([$R_3NH^+$]/[$R_3N$]$_0$) further support the hypothesis (FIG. 4B). The PEO segment did not change its peak intensity and was used as an internal standard. Throughout the ionization states, the proton resonance peaks for the PR segment of 5 were easily visualized although the peak intensity decreased with broadened peak width at higher pH, reflecting the bulk aggregation behavior of the copolymer. For 7, neutral state of the copolymer (i.e. 0%) led to completely suppressed resonance peaks in the PR segment due to the formation of highly compact micelle cores. Transmission electron microscopy (TEM) of 7 in aqueous solution demonstrated the formation of micelles above its pKa (6.7) at pH 7.4 and complete micelle dissociation at pH 5.5 (FIG. 4C). In comparison, no micelles were formed from 5 at either pH (data not shown).

In summary, these data suggested that hydrophobic micellization was the primary driving force for the observed cooperative deprotonation behavior of the ammonium groups in 7.

IV. Measurement of Critical Micelle Concentration (CMC) of PEO-b-PR Diblock Copolymers CMC of each PEO-b-PR copolymer was measured in the 0.2 M sodium phosphate buffer at pH 7.4. First, a copolymer stock solution (3 mg/mL) was diluted to different concentrations in the same buffer. In each solution, 54, pyrene in THF solution ($2\times10^{-4}$ mol/L) was added to 2 mL polymer solution to produce the final pyrene concentration at $5\times10^{-7}$ mol/L. The fluorescence spectra were recorded on a Hitachi fluorometer (F-7500 model) with the excitation wavelength of 339 nm and the excitation and emission slits at 10.0 nm and 1.0 nm, respectively. The $I_1$ and $I_3$ values were measured as the maximum emission intensity at ca. 372 and 382 nm, respectively. $I_1/I_3$ ratio was plotted as a function of polymer concentration at different pH values. $I_1/I_3$ ratio reflects the polarity of the pyrene environment where partition of pyrene in the hydrophobic micelle core leads to decreased $I_1/I_3$ values (Kalyanasundaram et al., J. Am. Chem. Soc. 1977, 99:2039-2044; Winnik, Chem. Rev. 1993, 93:587-614). CMC values were measured as the threshold polymer concentration at which micelles were formed in solution. To avoid TMR interference, PEO-b-PR copolymers without TMR conjugation were used in these studies. The CMC values at pH 7.4 were listed in Table 3.

Example 3

Location and Mechanism of Intracellular pHAM (TMR Nanoprobes) Activation

I. Confocal Laser Scanning Microscopy in Human Lung Carcinoma Cells

To investigate the intracellular activations of pHAM, nanoprobe 3 in human H2009 lung cancer cells was examined by confocal laser scanning microscopy and the activation of pHAM nanoprobes in H2009 cells was quantified by relative fluorescence intensity (FIG. 5).

H2009 cells were cultured in RPMI 1640 medium (Invitrogen, Calif.) supplemented with 5% fetal bovine serum (FBS), 100 IU/mL penicillin and 100 μg/mL streptomycin at 37° C. in 5% CO2 atmosphere. For subcellular trafficking and colocalization studies, H2009 cells were transfected with baculovirus using Organelle Lights™ Endosomes-GFP and Lysosomes-GFP BacMam 1.0 kits (Molecular Probes, Ore.) for Rab5a (early endosome marker) and Lamp1 (late endosome/lysosome marker) labeling, respectively. Cells were then cultured in growth medium for further analysis. For confocal imaging studies of micelle uptake and intracellular activation, H2009 cells were plated in glass bottom dishes (MatTek, Mass.) in 2 mL complete RPMI medium and incubated with nanoprobe 3 at a polymer concentration of 0.2 mg/mL at pH 7.4. Confocal images were captured at 0, 15, 30, 45, and 60 min after addition of micelles. After 60 min incubation, 0.1 N HCl solution (250 μL) was added into medium to acidify the medium pH to 5.0 and cells were immediately imaged. The images were analyzed using Image-J software. Five independent measurements were presented as the mean±standard deviation. For colocalization experiments, transfected cells expressing Rab5a-GFP or Lamp1-GFP were seeded in glass bottom dishes in 2 mL complete RPMI medium without phenol red. After 24 hr cell growth, 0.4 mg of nanoprobe 3 or 4 (5 mg/mL copolymer solution) in PBS (pH 7.4) was added into medium to give a final polymer concentration of 0.2 mg/mL. Images were captured at designated time points by a Nikon ECLIPSE TE2000-E confocal microscope with a 100× objective lens. GFP and TMR were excited at 488 and 543 nm, respectively. The emission wavelengths of GFP and TMR were 515 and 595 nm, respectively.

Figures 5A, 5B:
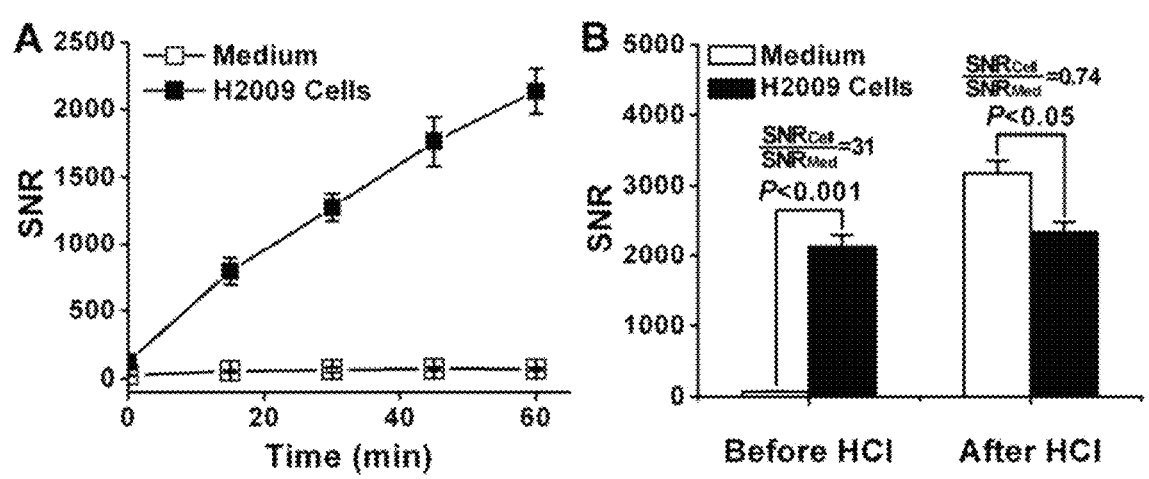
FIGS. 5A and 5B show quantification of activation of pHAM nanoparticles in H2009 cells and culture medium upon acidification.

Because pHAM nanoprobes are "silent" at neutral pH, they were directly applied in the culture medium and the kinetics of their internalization was monitored without the need to remove the medium. Right after the nanoprobe addition, neither the H2009 cells nor the medium showed observable fluorescence signal. At 15 min, punctuate fluorescent dots appeared inside the cells. The number of fluorescent dots increased over time. Signal to noise ratio of the H2009 cells ($SNR_{Cell}$, using fluorescence intensity at time 0 as the background noise) allowed further quantification of the increased nanoprobe uptake and activation over time. At 60 min, a 31-fold increase in $SNR_{Cell}$ (2.14±0.17× $10^3$) was observed over the medium ($SNR_{Med}$=69.3±9.1, P<0.001) where majority of the nanoprobes were still present (FIG. 5A). Then 0.1N HCl solution was added to acidify the medium pH to 5.0 and considerable increase in fluorescence intensity in the medium background was found. A reverse trend of fluorescence contrast was observed, where $SNR_{Cell}$ was 74% of $SNR_{Med}$ (P<0.05) (FIG. 5B).

These data illustrated that pHAM nanoprobes can dramatically increase the contrast sensitivity of cancer cells compared to potentially always ON nanoprobes (as in the case after HCl was added).

II. Activation of pHAM in Endocytic Organelles in Human Lung Cancer Cells

To further investigate whether different endocytic organelles can selectively activate pHAM, H2009 cells were transfected with green fluorescent protein (GFP)-fused Rab5a and Lamp I biomarkers in early endosomes and late endosomes/lysosomes, respectively.

H2009 cells were plated in glass bottom dishes (MatTek, Mass.) in 2 mL complete RPMI medium and incubated with nanoprobe 3 at a polymer concentration of 0.2 mg/mL at pH 7.4. Confocal images were captured at 0, 15, 30, 45, and 60 min after addition of micelles. After 60 min incubation, 0.1 N HCl solution (250 μL) was added into medium to acidify the medium pH to 5.0 and cells were immediately imaged. The images were analyzed using Image-J software. Five independent measurements were presented as the mean±standard deviation. For colocalization experiments, transfected cells expressing Rab5a-GFP or Lamp1-GFP were seeded in glass bottom dishes in 2 mL complete RPMI medium without phenol red. After 24 hr cell growth, 0.4 mg of nanoprobe 3 or 4 (5 mg/mL copolymer solution) in PBS (pH 7.4) was added into medium to give a final polymer concentration of 0.2 mg/mL. Images were captured at designated time points by a Nikon ECLIPSE TE2000-E confocal microscope with a 100× objective lens. GFP and TMR were excited at 488 and 543 nm, respectively. The emission wavelengths of GFP and TMR were 515 and 595 nm, respectively. For experiments on the inhibition of acidification of lysosomes with bafilomycin A1 and its effect on intracellular activation of nanoprobes 3 and 4, transfected H2009 cells expressing Lamp 1-GFP was seeded in glass bottom dishes in 2 mL complete RPMI 1640 medium without phenol red. After 24 h cell growth, the medium was replaced with fresh medium containing bafilomycin A1 (final concentration=1 μM) and cells were incubated at 37° C. for 1 h. Then, 0.4 mg of nanoprobe 3 or 4 in PBS (pH 7.4) was added into medium to give a final polymer concentration of 0.2 mg/mL. After incubation at 37° C. for 1 h, cells were imaged by a Nikon ECLIPSE TE2000-E confocal microscope with a 100× objective lens. GFP and TMR were excited at 488 and 543 nm, respectively. The emission wavelengths of GFP and TMR were 515 and 595 nm, respectively. After images captured, the medium was replaced by fresh medium. The cells were incubated at 37° C. for 5 h, followed by confocal microscopy analysis.

Figures 6A, 6B, 6C, 6D:
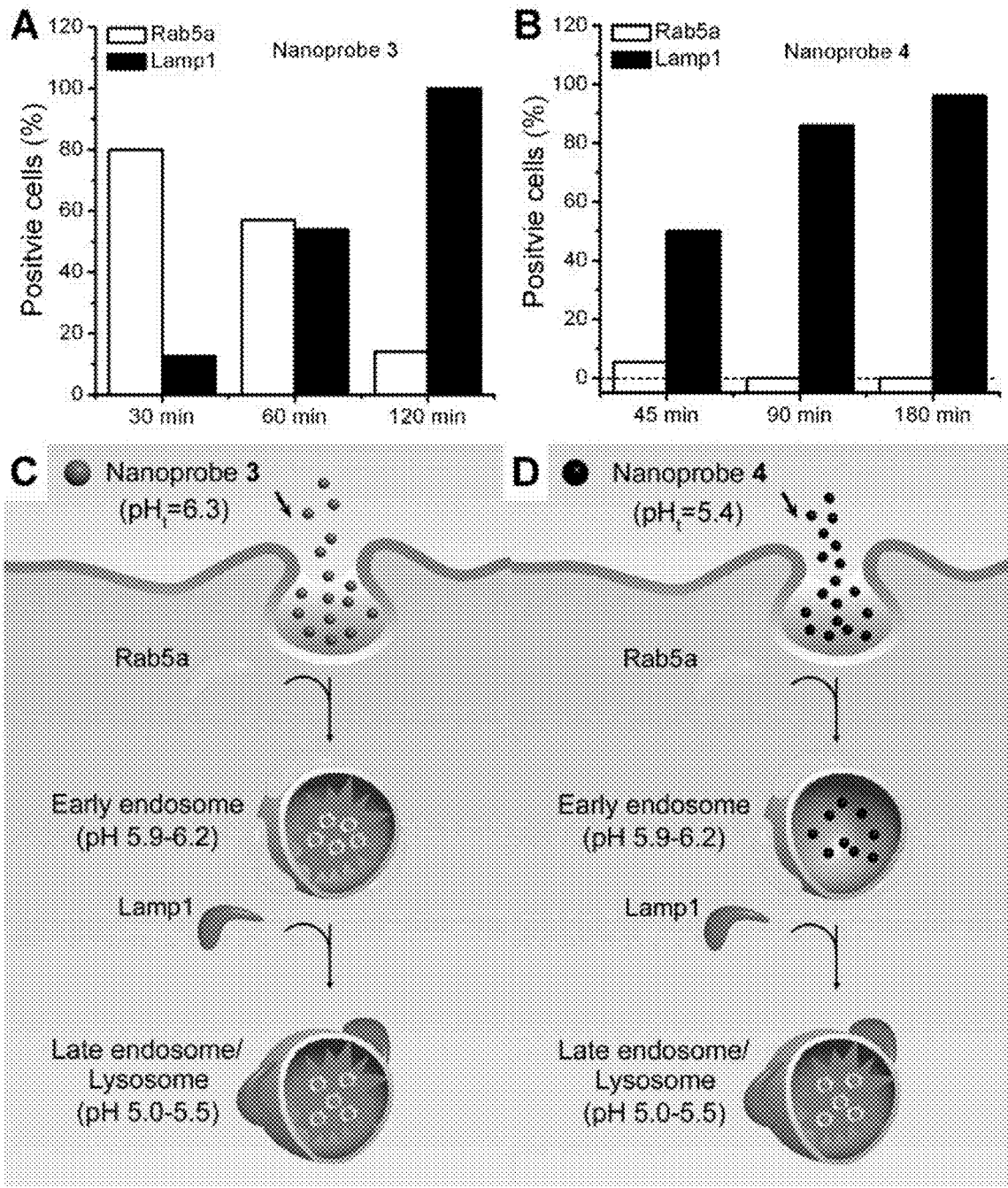
FIG. 6A shows an examination of the subcellular locations (early endosomes (Rab5a) and late endosomes/lysosomes (Lamp1)) for pHAM activation of nanoprobe 3 over time using confocal imaging.
FIG. 6B shows an examination of the subcellular locations (early endosomes (Rab5a) and late endosomes/lysosomes (Lamp1)) for pHAM activation of nanoprobe 4 over time using confocal imaging.
FIG. 6C and FIG. 6D depict the different processes of intracellular uptake and activation of the two nanoprobes.

Two pHAM nanoprobes (3 and 4 with $pH_t$ of 6.3 and 5.4, respectively) were incubated with H2009 cells and confocal imaging was used to examine the subcellular locations for pHAM activation. H2009 cells (N=30-50) with 20 or more colocalized dots (i.e. activated pHAM within early endosomes or lysosomes) were identified as positive and the percentage was quantified (FIGS. 6A and 6B). For nanoprobe 3, 80% of cells were positive in colocalization with early endosomes at 30 min, whereas only 12% colocalized with late endosomes/lysosomes. Over time, colocalization of activated 3 decreased with early endosomes but increased with late endosomes/lysosomes (FIG. 6A). In contrast, nanoprobe 4 ($pH_t$=5.4) showed a different pattern of subcellular location for activation. At all times, less than 10% of positive cells were found with early endosome colocalization. Instead, almost all the activated nanoprobe 4 colocalized with late endosomes/lysosomes (FIG. 6B). FIG. 6C and FIG. 6D depict the different processes of intracellular uptake and activation of the two nanoprobes. Nanoprobe 3 can be quickly activated inside early endosomes with higher vesicular pH (5.9-6.2) (Casey et al., *Nat. Rev. Mol. Cell Biol.* 2010, 11:50-61; Modi et al., *Nat. Nanotech.* 2009, 4:325-

330) and the activation is sustained as the nanoprobes traffic into late endosomes/lysosomes. By contrast, nanoprobe 4 is almost exclusively activated inside the late endosomes/lysosomes with lower vesicular pH (5.0-5.5) (Casey et al., *Nat. Rev. Mol. Cell Biol.* 2010, 11:50-61; Modi et al., *Nat. Nanotech.* 2009, 4:325-430). Similar results were also found with human SLK tumor endothelial cells (data not shown).

These data demonstrate the feasibility of targeting small differences in the vesicular pH inside different endocytic organelles by the pHAM nanoparticles.

To verify the intracellular activation mechanism of pHAM, H2009 cells were incubated with bafilomycin A1 for 1 hr and then added nanoprobe 3. Bafilomycin is a specific inhibitor of vacuolar-type $H^+$-ATPase (V-ATPase; Gagliardi et al., *Curr. Med. Chem.* 1999, 6:1197-1212.), which is responsible for the proton pumping across the plasma membranes and acidification of intracellular organelles (e.g. lysosomes). Data show that in the presence of bafilomycin A1, nanoprobe 3 was not activated as indicated by the absence of TMR fluorescence. After removal of bafilomycin A1 and 3 in the culture medium, the activation of 3 emerged with colocalization of TMR fluorescence with lamp 1-GFP labeled lysosomes. Similar results were also found with nanoprobe 4 in H2009 cells.

These experiments demonstrated that the synthesized nanoparticles are "silent" in the media at pH 7.4 but can be activated upon uptake into the cells. Moreover, nanoparticles with pH transitions at 6.3 and 5.4 can be selectively activated in different endocytic compartments such as early endosomes (pH 5.9-6.2) and lysosomes (5.0-5.5). These data demonstrate the feasibility of targeting small differences in the vesicular pH inside different endocytic organelles by the pHAM nanoparticles.

Example 4

Chemotherapeutic Encapsulation into pHAM Nanoparticles

This study sought to demonstrate that pHAM nanoparticles could encapsulate a high percentage of chemotherapeutics and subsequently quickly release it when exposed to an acidic environment similar to what is observed in tumor cells.

I. Encapsulation of Doxorubicin Into Micelles

PEO-b-PC6A was synthesized as above (see Example 1 (I and II)). Doxorubicin encapsulation in micelles was achieved by first dissolving doxorubicin and PEO-b-PC6A in water and hydrochloric acid. This solution was then added drop by drop into a 0.1M pH 9 buffer solution under sonication.

By using this method, doxorubicin loading percentages between 5 and 6 percent out of a theoretical loading of 10 percent were obtained. Drug loading was calculated by dissolving doxorubicin-encapsulated micelles in chloroform and then measure the UV-vis absorbance.

II. Release of Doxorubicin Upon Exposure to Acidic Environments

Doxorubicin release experiments were conducted by measuring the fluorescence intensity at different time points of the doxorubicin-loaded micelles in various pH environments. At first, 125 µL of doxorubicin-loaded micelles was mixed with 175 µL water in a cuvette, and an initial fluorescence spectrum was taken. Then, 10-20 µL of 5M pH buffer was added to the cuvette to measure the doxorubicin release over time. Drug concentration was calculated based on fluorescence calibration curves of free doxorubicin in water and pH buffer. At low concentrations (<0.025 mg/mL), fluorescence intensity and concentration are directly proportional. Fluorescence quenching occurs at higher concentrations.

Figure 7:
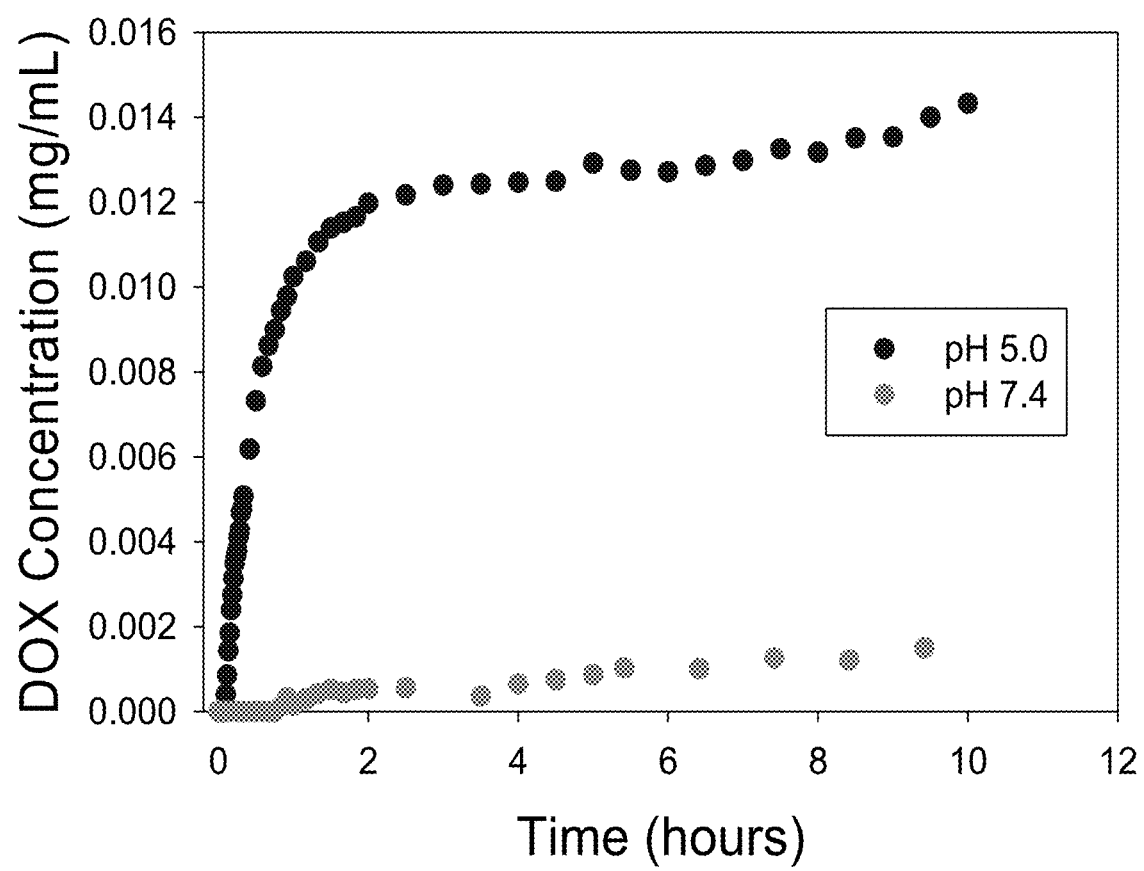
FIG. 7 shows doxorubicin release from PEO-b-PC6A micelles at different time points in various pH environments.

The release study shows that doxorubicin releases from the micelles rapidly at pH 5.0 and that the micelles at pH 7.4 are relatively stable. At pH 5.0, the micelles release doxorubicin rapidly in the first two hours and afterwards, the release is very slow. At pH 7.4, doxorubicin slowly releases out of the micelles after several hours, but the majority of the drug remains encapsulated (FIG. 7). At low concentrations (<0.025 mg/mL), fluorescence intensity and concentration are directly proportional. Fluorescence quenching occurs at higher concentrations.

This study demonstrated that polymeric micelles can encapsulate a high percentage of doxorubicin (~6%) and that polymers that are protonated in acidic conditions can dissociate much faster than polymers that undergo hydrolysis at low pH values. Release studies showed that the micelles can release doxorubicin rapidly at pH 5.0, with the majority of the drug released in the first two hours.

III. Encapsulation of Paclitaxel into Micelles

Paclitaxel-loaded micelles were prepared according to a previously published procedure. In brief, 20 mg of MeO-PEO5k-PDPA25k and 2 mg of paclitaxel were dissolved in 1 mL THF. Then, the mixture was rapidly added into 10 mL of Milli-Q water under sonication. The mixture was ultrafiltrated for more than 6 times to remove THF using the micro-ultrafiltration system. The resulting micellar solution was placed at room temperature for 4 hour and filtrated through a 0.45 µm cellulose membrane to remove any precipitates in micelle solution. Paclitaxel loading content in polymeric micelles was determined by disintegrating of micelles in acetonitrile. Paclitaxel concentration was determined by HPLC using a reversed-phase $C_{18}$ column (5 µm, 4.6×250 mm) with a mobile phase consisting of 34% acetonitrile and 66% water at 227 nm at the flow rate of 1 mL/min. Paclitaxel content in MeO-PEO5k-PDPA25k micelles was 8.3±0.6%.

Example 5

Figure 8:
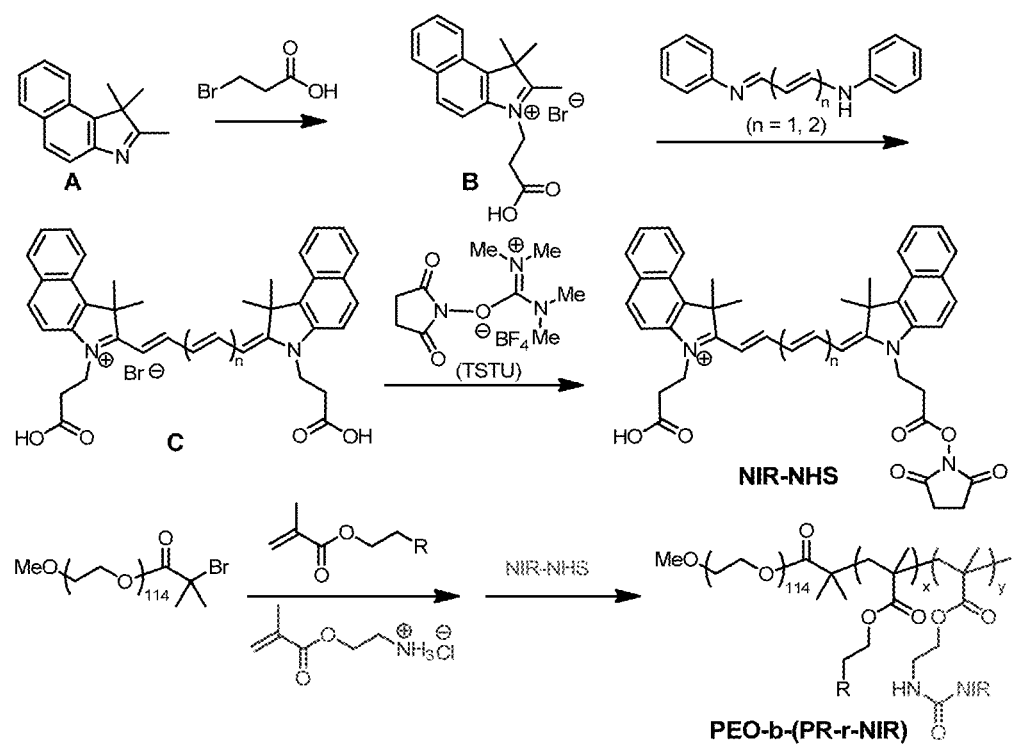
FIG. 8 illustrates syntheses of NIR-NHS ester and PEO-b-(PR-r-NIR) copolymers for the development of NIR-pHAM.

Generation of a pHAM-NIR Fluorophores Comprising Cypate for Tumor Angiogenesis Imaging I. Synthesis of NIR-pHAM Cypate-NHS esters (an NIR dye) were synthesized following published procedures (FIG. 8; Lopalco, et al., *Org. Biomol. Chem.*, 2009, 7:856-859; Ye et al., *Bioconjug. Chem*, 2007, 19:225-234). FIG. 8 shows a representative synthetic scheme of NIR-NHS and PEO-b-(PR-r-NIR) copolymers. Reaction of 1,2,2-trimethyl-1H-benz[e]indole (A) with 3-bromopropanoic acid in 1,2-dichlorobenzene at 110° C. yielded B. Further reaction of B with malonaldehyde bis(phenylimine) monohydrochloride (n=1) or glutaconaldehyde dianil monohydrochloride (n=2) yielded the corresponding NIR fluorophores (C). Treatment of C with O—(N-succinimidyl)-1,1,3,3-tetramethyluronium tetrafluoroborate (TSTU) and N,N-diisopropylethylamine (DIEA) in dry DMF yielded NIR-NHS ester. Finally, the PEO-b-(PR-r-NIR) was synthesized through conjugation of NIR-NHS onto the block copolymers bearing the primary amino groups. In the cypate-containing copolymers, the number of repeating units in the PR block was 70. After syntheses, polymers were fully characterized by gel permeation chromatography, $^1$H NMR, and fluorescence spectroscopy. Useful analogs with different excitation/emission wavelengths (e.g. $\lambda_{ex}/\lambda_{em}$=678/704 nm when n=1; $\lambda_{ex}/\lambda_{em}$=781/808 nm when n=2) were subsequently produced.

II. Optimization of NIR-pHAM Fluorophores

Preliminary studies on TMR-pHAM show that PR length and TMR number may affect the ultra-pH response. Adequate PR length may provide for cooperative micellization and directly affects pH response, i.e. $\Delta pH_{10-90\%}$. The TMR density may control the fluorescence response. For example, an optimal $F_{max}/F_{min}$ of 55 was achieved for TMR nanoprobe 3 at y=3 without the observable intramolecular fluorescence quenching at the ON state. In comparison, at y=1, only a $F_{max}/F_{min}$ of 10 was obtained (data not shown).

For the NIR-pHAM development, the PR length (70) is maintained to investigate the optimal NIR density per polymer chain. It is anticipated that different fluorophores (i.e. cypate vs. TMR) have different homoFRET and PET quenching effects, which may affect the optimal pHAM composition. To quantify the contributions from homoFRET and PET, a NIR-conjugated polymer is blended with NIR-free polymer and systematically the molar ratios of NIR-conjugated polymer are varied. Extrapolation of quenching coefficient to one NIR dye per micelle permits the quantification of PET contribution. The cypate density (e.g. y=1, 3, 6) on the PR segment is then systematically increased. Quenching efficiency is measured and correlated with the homoFRET model (Lakowicz (ed.), *Principles of Fluorescence Spectroscopy*, Edn. 3$^{rd}$, 443-475 (Springer, New York City; 2006), which is inversely proportional to $r^6$ (r is the distance between the dye pairs in the micelle core).

A tunable set of NIR-pHAM (i.e. nanoprobes 3, 4, 6, 7, where TMR is replaced with NIR dye) nanoprobes with pH transitions at 5.4, 6.3, 6.8 and 7.2, respectively is then synthesized. Slight variations of $pH_t$ may result when a different dye (e.g. cypate) is used. After NIR-pHAM syntheses, pH and fluorescence responses (e.g. $pH_t$, $\Delta pH_{10-90\%}$, $F_{max}/F_{min}$, as described previously), article size (TEM and DLS), critical micelle concentration and fluorescence life times are measured.

Example 6

Development of Vascular-Targeted cRGDfK-pHAM

This study demonstrates the development of cRGDfK-pHAM to target pH sensitive polymeric micelle nanoparticles to the vasculature of tumors. The small peptide ligand cRGDfK (cRGD) specifically targets αvβ3 integrins (CD61) which are over-expressed in angiogenic tumor endothelial cells.

Figure 9:
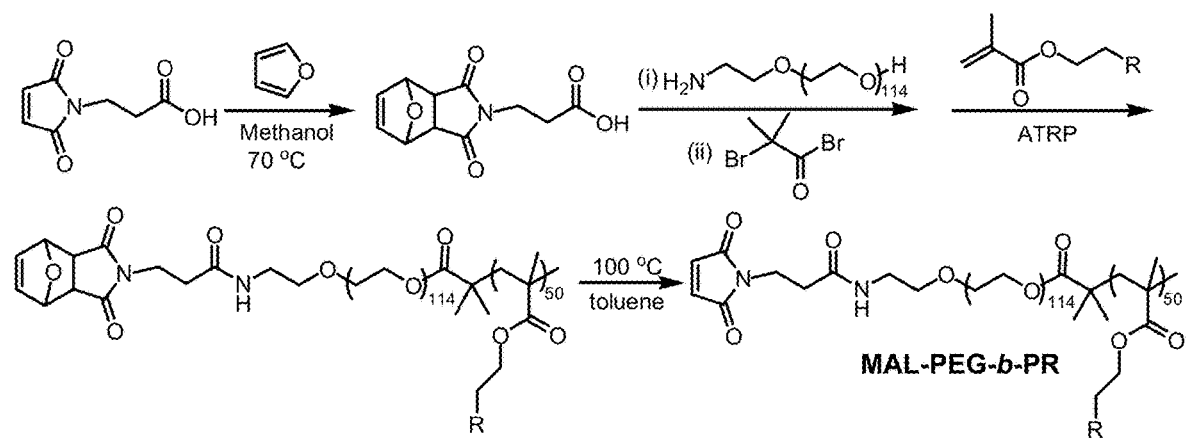
FIG. 9 illustrates syntheses of maleimide-terminated PEG-b-PR copolymers.

Thiol-maleimide chemistry was used for ligand conjugation on the pHAM surface (FIG. 9). MAL-PEO-b-PR was mixed with PEO-b-(PR-r-NIR) at 10 mol % molar ratio of MAL-PEO-b-PR. After micelle formation, cRGD-SH peptides were conjugated via thiol-maleimide linkage. The peptide conjugation was monitored by the disappearance of maleimide group (6.7 ppm) and formation of the aromatic group (7.0-7.5 ppm) from D-Phe on the cRGDfK by the $^1$H NMR. Amino acid analysis was further used to quantify the peptide density on the surface of pHAM nanoprobes (Khemtong, et al., *Cancer Res.*, 2009, 69:1651-1658). TEM and DLS was used to examine the ligand functionalization on the particle size and morphology, and fluorescence spectrophotometry was used to verify the pH-responsive fluorescence properties of pHAM. Laser scanning confocal microscopy was the primary tool to examine the kinetics of cell uptake and intracellular activation of the targeted pHAM.

Human umbilical vascular endothelial cells (HUVECs) were used in these studies. This cell line is well accepted as a cell culture model in vitro for angiogenic endothelial cells and αvβ3 integrin is over-expressed on HUVEC cells (Ellis et al., *J. Vasc. Res.*, 2003, 40:234-243; Vag et al., *Contrast Media Mol. Imaging*, 2009, 4:192-198). FIG. 10 shows the contrast specificity of cRGD-encoded PEG-b-(PDPA-r-NIR) pHAM (pH transition=6.3) in HUVEC cells. The surface density of cRGD/cRAD was controlled at 20 mol %. To examine αvβ3-specificity, cRAD-encoded pHAM and free cRGD block+cRGD-encoded pHAM were used as controls. HUVEC cells were cultured in EGM medium prior to incubation of different pHAM samples (polymer concentration: 0.2 mg/mL) for 3 hrs. In the cRGD block control, 20 molar excess of free cRGD peptides were co-incubated with cRGD-pHAM to compete for αvβ3 binding. Because pHAM is silent at medium pH, activation of pHAM inside HUVEC cells can be directly imaged without the need to remove the medium.

Figures 10A, 10B:
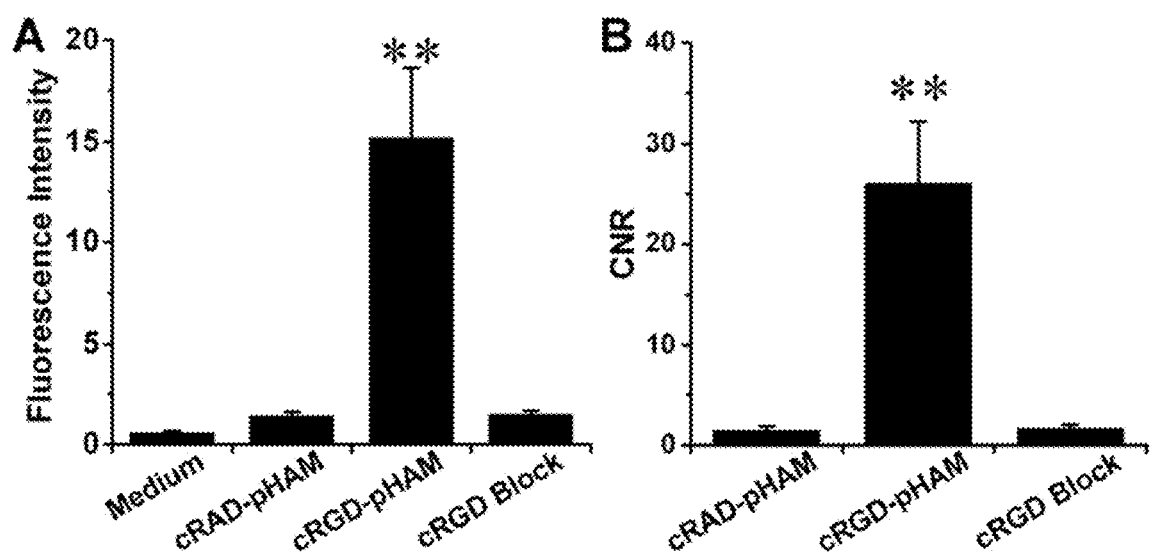
FIG. 10A shows fluorescence intensity of HUVEC cells differently treated with cRGD-encoded pHAM nanoprobes, cRAD-pHAM, free cRGD block (N>10 for each group) and cell culture medium, respectively.
FIG. 10B shows contrast to noise ratio (CNR) of HUVEC cells treated with cRGD-pHAM over the cRAD-pHAM and dRGD block controls.

The data demonstrated that after cell incubation, cRGD-pHAM showed dramatically increased fluorescence intensity inside HUVEC cells. In comparison, cRAD-pHAM and cRGD block controls showed little fluorescence signals. ROI analyses of different HUVEC cells showed the average fluorescence intensity was 15.2±3.5, 1.4±0.2, 1.5±0.2 for cRGD-pHAM, cRAD-pHAM, and cRGD block control, respectively (FIG. 10A). The fluorescence for the medium background of similar ROI size was 0.56±0.09. The culture medium was used as the background noise to calculate the contrast over noise ratio (CNR=(FIpHAM-FImed)/FImed, where FIpHAM and FImed are the fluorescence intensity of pHAM sample and medium, respectively) for different pHAM conditions. The values of CNR were 26.1±6.2, 1.5±0.4, and 1.6±0.4 for cRGD-pHAM, cRAD-pHAM, and cRGD block control, respectively (FIG. 10B). It is worth noting that >10-fold increase in CNR for cRGD-pHAM was observed over the two controls, indicating αvβ3-specific targeting (P<0.01). In particular, this contrast was observed in the presence of a high concentration (0.2 mg/mL) of "silent" pHAM nanoprobes in the cell culture medium.

Example 7

Evaluation of the Specificity and Efficacy of Targeted pHAM in the Imaging of Distinctive Angiogenesis Biomarkers in Tumor-Bearing Mice In Vivo I. pHAM Activation in the Tumor Vasculature Since TMR has short excitation/emission wavelengths ($\lambda_{ex}$=540 nm, $\lambda_{em}$=580 nm), these studies used cRGD-encoded, TMR-conjugated pHAM nanoparticles to demonstrate pHAM activation in tumor vasculature.

Athymic nude mice bearing A549 tumor xenografts (100-200 mm$^3$, n=3 for each group) were used in these studies. cRGD- and cRAD-encoded PEG-b-(PDPA-r-TMR) pHAM nanoprobes were used with 20 mol % surface density. Nanoprobes were injected at 14 μmol TMR/kg dose via the tail vein and animals were sacrificed 3 hrs after pHAM injection. Various organs were removed and placed on a Petri dish and imaged by IVIS Spectrum.

TMR signals of the explanted organs and tumor tissues from cRAD-encoded and cRGD-encoded TMR-pHAM can be directly observed by a Maestro fluorescence imaging instrument with identical imaging conditions. Despite the limited tissue penetration of TMR, tumor from cRGD-encoded pHAM clearly showed higher fluorescence intensity than that from cRAD-encoded pHAM, as well as the adjacent muscle tissues. In both groups, the blood drops did not show any fluorescence signals, demonstrating the intended background suppression effect of pHAM in blood. Meanwhile, liver appeared to be the major organ that took up both pHAM formulations, consistent with the RES clearance of nanosized particles (Moghimi, et al., *Pharmacol. Rev.,* 2001, 53:283-318).

After ex vivo imaging, tumor tissues were frozen and sectioned at 8 μm. Confocal imaging of tumor tissues showed a remarkable increase of fluorescence intensity in cRGD-pHAM treated tumor than cRAD-pHAM control. To verify the location of pHAM activation, tumor sections were first stained with rat primary anti-mouse mAb against PECAM (CD31), followed by washing and staining with Delight 488-conjugated anti-rat secondary antibody. Overlay images show that majority of pHAM activation co-localized with the vasculature stain, indicating the active targeting and activation of cRGD-encoded pHAM in the tumor vasculature. This study demonstrates the feasibility of targeting specific angiogenesis biomarkers (i.e. $\alpha_v\beta_3$) by cRGD-encoded pHAM in tumor-bearing mice. To overcome the short tissue penetration of TMR dye, NIR-pHAM nanoprobes (e.g. cypate, λex/λem=781/808 nm when n=2) may be used for further animal studies in vivo.

II. Evaluation of Targeted NIR-pHAM Nanoprobes with Optimal $pH_t$ Values

The influence of $pH_t$ on the imaging specificity of angiogenesis biomarkers is investigated. In this series of studies, cRGD-encoded NIR-pHAM is used as a model system and cRAD-encoded NIR-pHAM as a control. NIR-conjugated PEG-b-PDBA ($pH_t$=5.4), PEG-b-PDPA (6.3), or PEO-b-PC7A (6.8) nanoprobes are evaluated. cRGD-pHAM nanoprobes with larger $pH_t$ values (e.g. 6.8) may lead to faster fluorescence response time inside early stage endosomes. However, it may also be more susceptible to be "activated" by other non-$\alpha_v\beta_3$ related mechanisms, such as acidic pH in tumor microenvironment. Vice versa, cRGD-pHAM with lower $pH_t$ values (e.g. 5.4) can be more specifically turned "ON" via $\alpha_v\beta_3$-mediated endocytosis; however, it may take longer time for them to be activated in angiogenic endothelial cells.

In this series of experiments, we inject the cRGD- and cRAD-encoded NIR-pHAMs with different $pH_t$ via the tail veins of mice bearing A549 tumors. The fluorescence intensity of tumors and other organs are recorded over time to examine the kinetics of pHAM activation. Living Image 4.0 software is used to display the 3D volume images superimposed with mouse anatomy. For tumor tissues, the fluorescence intensity is plotted over time to examine whether saturation kinetics is present for cRGD-encoded NIR-pHAM (as expected from receptor saturation). If saturation kinetics is observed, the optimal pHAM dose as the minimal dose that allows for receptor saturation is determined. This dose is then used in subsequent studies to minimize non-specific uptake in other organs (e.g. liver). The CNRs of tumors over the surrounding muscle tissues for cRGD-encoded vs. cRAD-encoded NIR-pHAM is then calculated and compared to investigate the target-specific contrast due to $\alpha_v\beta_3$-mediated endocytosis. For NIR-pHAMs with different $pH_t$ values, CNRs between the targeted (i.e. cRGD-encoded) and non-targeted (i.e. cRAD-encoded) groups across different NIR-pHAM designs is compared. These results are correlated with data on stealth pHAM (PEO surface) activation in tumor microenvironment. This results of this study selects the most optimal $pH_t$ design for NIR-pHAM to image specific angiogenesis biomarkers in vivo.

cRGD-encoded NIR-pHAM (NIR-conjugated PEG-b-PDPA ($pH_t$=6.3)) was used as a model system and non-targeted NIR-pHAM as a control. The NIR-conjugated PEG-b-PDPA had the structure of Formula I with the following:

| R' | R1/R2 | n | z | R'' | m | x | y | L | R''' |
|---|---|---|---|---|---|---|---|---|---|
| —CH₃ | iPr/iPr | 2 | 114 | —CH₃ | 2 | 70 | 3 | Cypate Cy5.5 | Br |

The targeted NIR-conjugated PEG-b-PDPA had 10 mol % surface density of cRGD.

cRGD-encoded and non-targeted NIR-conjugated PEG-b-PDPA were intravenously injected via the tail veins of athymic nude mice bearing A549 lung tumors. The in vivo NIR fluorescence intensity was recorded 3 hours postinjection. In a comparison group, a blocking dose of cRGDfK peptide was injected 30 min prior to the cRGD-encoded NIR-conjugated PEG-b-PDPA administration.

The tumor from cRGD-encoded NIR-conjugated PEG-b-PDPA clearly showed higher fluorescence intensity than that that from non-targeted NIR-conjugated PEG-b-PDPA or the cRGD blocking group.

III. Pharmacokinetics Studies of cRGD-Encoded pHAM

This study showed the blood circulation time of cRGD-encoded pHAM (targeted micelles) and cRGD-free pHAM (nontargeted micelles) in A549 tumor-bearing mice.

Female athymic nude mice (20-25 g) were inoculated s.c. on the right flank with human non-small cell lung cancer A549 cells (5×10⁶ cells/mouse). Tumors were allowed to reach 200-300 mm³ before injection of micelles. For PK studies, cRGD-free pHAM or 10% cRGD-encoded PEG-b-(PDPA-r-TMR) pHAM were injected at a dose of 20 mg/kg micelles through the tail vein. Blood was collected at 2 min, 3, 6, 12, 24 and 48 hours after i.v. injection. Plasma was isolated from RBCs by centrifugation at 1,000 rpm for 10 min. The plasma was stored at 4° C. for further analysis. Polymer was extracted from plasma with acidic methanol (0.1 M HCl:MeOH, 3:7, v/v) and detected with a fluorometer using excitation and emission wavelengths of 545 and 580 nm, respectively.

Figure 11:
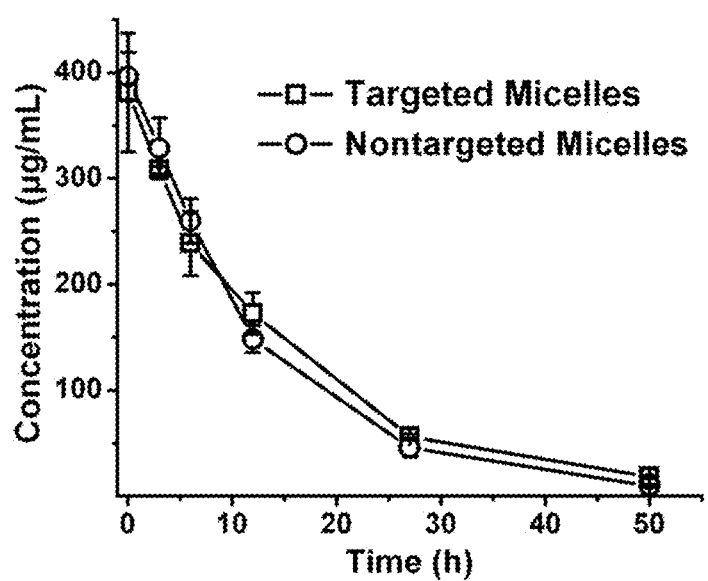
FIG. 11 shows the in vivo pharmacokinetics studies of cRGD-encoded pHAM (targeted micelles) and cRGD-free pHAM (nontargeted micelles) in A549 tumor-bearing mice.

Both cRGD-encoded pHAM and cRGD-free pHAM displayed prolonged blood circulation time. The blood half lives of cRGD-encoded pHAM and cRGD-free pHAM wer 10.0 and 9.5 hours, respectively (FIG. 11).

IV. Testing the Generality of NIR-pHAM Nanoplatform in Imaging $\alpha_v\beta_3$ Integrin and VEGFR2 in Several Tumor Xenograft Models NIR-pHAM formulation with the optimal $pH_t$ is used in these studies. For the VEGFR2-targeted nanoprobes, we purify the Fab$_{R2}$'-SH fragment of RAFL-1 mAb for NIR-pHAM conjugation. A non-specific Fab'-SH is also prepared from control rat IgG. Fab'-SH is conjugated to the NIR-pHAM surface via thiol-maleimide chemistry. RAFL-1-NIR immuno conjugate is used as the always ON control. For the $\alpha_v\beta_3$-targeted NIR-pHAM, cRGD-NIR as a small molecular dye conjugate is also synthesized. It is expected that these always ON probes have elevated blood signals with limited imaging payload increase at the targeted site, which have significantly less contrast sensitivity compared to the corresponding NIR-pHAM nanoprobes.

The targeted nanoprobes are investigated in other more clinically relevant tumor models in an orthotopic MDA-MB-231 breast tumor model in the mammary pad of female nude mice (Ran et al., *Neoplasia,* 2003, 5:297-307) orthotopic MiaPaca-2 pancreatic tumor model in nu/nu mice (Korpanty et al., *Cancer Res.,* 2007, 13:323-330). Both tumor models express high levels of angiogenesis biomarkers (e.g. VEGFR2, α$_v$β$_3$, endoglin). Imaging specificity and efficacy of NIR-pHAM nanoprobes in these tumor models is evaluated and results are validated by immunohistochemistry of these angiogenesis biomarkers in tissue sections.

Example 8

Evaluation of Activation of Non-Targeted NIR-pHAM in Acidic Tumors

Extracellular pH is becoming an important physiological parameter to study tumor microenvironment and metabolism. (Cardone et al., *Nature Rev. Cancer,* 2005, 5:786-795; Gerweck & Seetharaman, *Cancer Res.* 1996, 56:1194-1198; Helmlinger et al., *Nature Medicine,* 1997, 3:177-182). Aerobic glycolysis (aka, Warburg effect), conversion of glucose to lactic acid in the presence of oxygen, is uniquely observed in cancers. To maintain a healthy intracellular pH (~7.2), cancer cells utilize several transport systems (e.g. Na$^+$/H$^+$ exchange, vacuolar ATPases (V-ATPase), Na$^+$/HCO$_3^-$ exchange) to export the protons from inside cells. This results in microenvironmental acidosis that further facilitates cancer invasion through ECM degradation and promotion of angiogenesis.

Prior to studying the pHAM activation, the map in tumors is first measured using MRI relaxometry method for imaging of tissue pH in vivo (Garcia-Martin et al., *Magn. Reason. Med.,* 2006, 55:309-315; Raghunand et al., *Magn. Reason. Med.,* 2003, 49:249-257). After measurement by MRI the activation of non-targeted NIR-pHAM in the tumor microenvironment is evaluated. Due to the small size of pHAM (diameter 40-50 nm), they accumulate in the tumor interstitium through the leaky tumor microvasculature. In a typical experiment, NIR-pHAM nanoprobes are injected via the tail vein. 3D activation map and dynamic contrast over time are measured on the IVIS Spectrum. Living Image (4.0) software provided by the manufacturer is used to analyze the spatial and temporal activation of NIR-pHAM nanoprobes. Moreover, the quantitative 3D fluorescence (FLIT4) toolset is used to co-register the optical images with the map from MRI. The pattern of pHAM activation with the map in tumors is then compared. The NIR-pHAM activation profiles are examined and compared for nanoprobes with different pH transitions (i.e. 5.4, 6.3, 6.8, 7.2).

The experiments show the following: (1) closely correlated pH$_e$ and pH$_i$ relationships between the tumor microenvironmental pH and NIR-pHAM activation, respectively; (2) for NIR-pHAM with high pH transitions (i.e. 6.8 or 7.2), because of the ultra-pH response of the tested pHAM nanoprobes (i.e. <0.25 pH unit for OFF/ON transitions), they are highly sensitive imaging probes for acidic tumors and are useful for tumor drug delivery; and (3) for NIR-pHAM with low pH transitions (i.e. 5.4 or 6.3), their lack of activation by the acidic tumor microenvironment results in achieving the imaging specificity for angiogenesis biomarkers.

PEG-PC7A-Cy5.5 nanoprobes were tested. The structure of PEG-PC7A-Cy5.5 utilized had the structure of Formula I with the following:

| R' | R1/R2 | n | z | R" | m | x | y | L | R''' |
|---|---|---|---|---|---|---|---|---|---|
| —CH$_3$ | —(CH$_2$)$_6$— | 2 | 114 | —CH$_3$ | 2 | 70 | 3 | Cypate Cy5.5 | Br |

PEG-PC7A-Cy5.5 nanoprobes (pH$_f$=6.7) were intravenously injected (25 mg/kg) via the tail vein of athymic nude mice bearing A549 lung tumors. In the comparison group, α-cyano-4-hydroxycinnamate, a monocarboxylate transferase 1 (MCT1) inhibitor, was injected 24 hours prior to nanoprobe administration. The tumor from the non-targeted PEG-PC7A-Cy5.5 nanoprobes clearly showed higher fluorescence intensity than that from the MCT1 inhibitor group.

Example 9

Development of VEGFR2-Targeted pHAM

This study demonstrates the development of Fab$_{R2}$'-functionalized micelles for specific targeting of VEGFR2 receptors on the surface of endothelial cells. The Fab' fragment of RAFL-1 mAb is used for specific targeting to VEGFR2 receptors since VEGFR2 is over-expressed in angiogenic tumor endothelial cells. RAFL-1 mAb binds to VEGFR2 with high affinity (15 pM) and specificity (Ran et al., *Neoplasia,* 2003, 5:297-307) and, following purification of the Fab$_{R2}$'-SH fragment of RAFL-1 for surface functionalization, Fab$_{R2}$'-functionalized liposomes showed >30-fold increase in cell uptake in mouse endothelial cells over the control liposomes (Marconescu, *PhD. Thesis,* UT Southwestern Medical Center, Dallas, 2008). Compared with the whole mAb, Fab$_{R2}$'-SH has the advantage of introducing a smaller targeting moiety (50 vs. 150 kD), and superior presentation of binding epitope on the pHAM surface (i.e. facing solution instead of random orientation for whole mAb).

Thiol-maleimide chemistry is used for ligand conjugation on the pHAM surface. MAL-PEO-b-PR is mixed with PEO-b-(PR-r-NIR) at different molar ratios (e.g. 20 mol % of MAL-PEO-b-PR). For each pHAM copolymer, its corresponding maleimide-terminated copolymer is then synthesized (FIG. 8). After micelle formation, Fab$_{R2}$'-SH peptides are conjugated via thiol-maleimide linkage. Amino acid analysis is further used to quantify the peptide density on the surface of pHAM nanoprobes (Khemtong, et al., *Cancer Res.,* 2009, 69:1651-1658). TEM and DLS is used to examine the ligand functionalization on the particle size and morphology, and fluorescence spectrophotometry is used to verify the pH-responsive fluorescence properties of pHAM. Laser scanning confocal microscopy is the primary tool to examine the kinetics of cell uptake and intracellular activation of the targeted pHAM.

The invention claimed is:
1. A block copolymer capable of forming a pH-sensitive micelle comprising a compound of Formula (I):

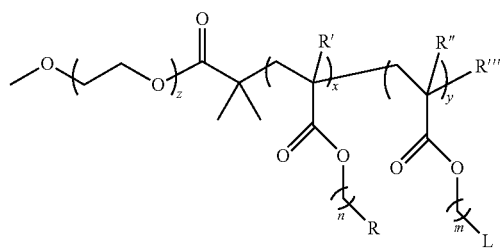

(Formula I)

wherein R is —NR$^1$R$^2$, wherein R$^1$ and R$^2$ are straight alkyl groups, wherein R$^1$ and R$^2$ are the same or different, wherein $R^1$ and $R^2$ together have from 5 to 16 carbons, and wherein $R^1$ and $R^2$ may optionally join to form a ring;
L is a labelling moiety;
R' is —H or —CH3;
n is 1 to about 10;
m is 1 to about 10;
x is about 20 to about 200 in total;
y is 0 to about 6;
wherein z is such that the PEO is about 2 kD to about 20 kD in size;
wherein R'" is any suitable moiety; and
wherein the following portion of the structure:

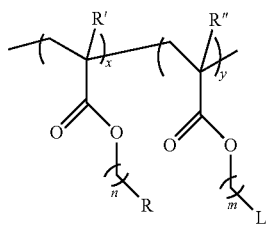

may be arranged in any order.

2. The block copolymer of claim 1, wherein the micelles have a pH transition range of less than about 1 pH unit.

3. The block copolymer of claim 1, wherein n is 2 and $R^1$ and $R^2$ is n-Bu.

4. The block copolymer of claim 3, wherein the micelles have a pH transition value of about 5.4.

5. The block copolymer of claim 1, wherein n is 2 and $R^1$ and $R^2$ join to form a ring having —$(CH_2)_5$—.

6. The block copolymer of claim 5, wherein the micelles have a pH transition value of about 7.2.

7. The block copolymer of claim 1, wherein n is 2 and $R^1$ and $R^2$ join to form a ring having —$(CH_2)_6$—.

8. The block copolymer of claim 7, wherein the micelles have a pH transition value about 6.8.

9. The block copolymer of claim 1, wherein the block copolymer has a polydispersity index of less than 1.2.

10. The block copolymer of claim 1, wherein the block copolymer has a polydispersity index of less than 1.1.

11. The block copolymer of claim 1, wherein the micelles have a size of about 10 to about 200 nm.

12. The block copolymer of claim 1, wherein the micelles have a size of about 20 to about 100 nm.

13. The block copolymer of claim 1, wherein the micelles have a size of about 30 to about 50 nm.

14. The block copolymer of claim 1, wherein L is a fluorescent label.

15. The block copolymer of claim 1, wherein the NIR label is cypate or a cypate analog.

* * * * *